(12) United States Patent
Borovinskih et al.

(10) Patent No.: US 10,136,964 B2
(45) Date of Patent: Nov. 27, 2018

(54) AUTOMATIC PLACEMENT OF PRECISION CUTS

(71) Applicant: Align Technology, Inc., San Jose, CA (US)

(72) Inventors: Artem Borovinskih, San Jose, CA (US); Anton Terekhov, Moscow (RU); Rene Sterental, Palo Alto, CA (US); Mikhail Minchenkov, Kratovo (RU); Ivan Pavlov, Cherepovets (RU)

(73) Assignee: Align Technology, Inc., San Jose, CA (US)

( * ) Notice: Subject to any disclaimer, the term of this patent is extended or adjusted under 35 U.S.C. 154(b) by 263 days.

(21) Appl. No.: 15/219,779

(22) Filed: Jul. 26, 2016

(65) Prior Publication Data

US 2016/0331492 A1    Nov. 17, 2016

Related U.S. Application Data

(62) Division of application No. 14/148,453, filed on Jan. 6, 2014, now Pat. No. 9,433,477, which is a division
(Continued)

(51) Int. Cl.
*A61C 3/00* (2006.01)
*A61C 7/00* (2006.01)
(Continued)

(52) U.S. Cl.
CPC .............. *A61C 7/002* (2013.01); *A61C 7/08* (2013.01); *A61C 7/36* (2013.01); *A61C 19/05* (2013.01);
(Continued)

(58) Field of Classification Search
CPC .............................................. A61C 7/00–7/36
(Continued)

(56) References Cited

U.S. PATENT DOCUMENTS 2,467,432 A    4/1949  Kesling
3,407,500 A   10/1968  Kesling
(Continued)

FOREIGN PATENT DOCUMENTS

AU    3031677 A    5/1979
AU     517102 B2   7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Yogesh Patel
(74) *Attorney, Agent, or Firm* — Wilson Sonsini Goodrich & Rosati

(57) ABSTRACT

An orthodontic positioning device and methods for making an orthodontic positioning device including a first patient removable orthodontic tooth positioning appliance having teeth receiving cavities shaped to receive and apply a resilient positioning force to a patient's teeth provided in one of an upper jaw and a lower jaw. The first appliance includes a hook configured to receive an orthodontic elastic band. The orthodontic positioning device also includes a second patient removable orthodontic tooth positioning appliance having teeth receiving cavities shaped to receive and apply a resilient positioning force to a patient's teeth provided in the other of the upper jaw and the lower jaw. The second appliance includes a cutout operable to expose an orthodontic elastic band receiving member.

7 Claims, 24 Drawing Sheets

Related U.S. Application Data of application No. 13/270,171, filed on Oct. 10, 2011, now Pat. No. 8,641,414.

(51) Int. Cl.
  *A61C 7/08* (2006.01)
  *A61C 7/36* (2006.01)
  *A61C 19/05* (2006.01)
  *B33Y 80/00* (2015.01)

(52) U.S. Cl.
  CPC ......... *A61C 2007/004* (2013.01); *B33Y 80/00* (2014.12)

(58) Field of Classification Search
  USPC ...................................................... 433/6–24
  See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,672 A * | 3/1985 | Kurz ...................... A61C 7/08 433/6 |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,683,244 A * | 11/1997 | Truax ...................... A61C 7/00 433/24 |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |

(56) References Cited

U.S. PATENT DOCUMENTS

| | | | |
|---|---|---|---|
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,450,807 B1 | 9/2002 | Chishti et al. | |
| 6,482,298 B1 | 11/2002 | Bhatnagar | |
| 6,524,101 B1 | 2/2003 | Phan et al. | |
| 6,554,611 B2 | 4/2003 | Shishti et al. | |
| 6,572,372 B1* | 6/2003 | Phan | A61C 7/00 433/18 |
| 6,629,840 B2 | 10/2003 | Chishti et al. | |
| 6,705,863 B2 | 3/2004 | Phan et al. | |
| 6,722,880 B2 | 4/2004 | Chishti et al. | |
| 6,932,598 B1 | 8/2005 | Anderson | |
| 6,935,858 B2 | 8/2005 | Cleary | |
| 8,641,414 B2 | 2/2014 | Borovinskih et al. | |
| 9,675,427 B2* | 6/2017 | Kopelman | A61C 7/08 |
| 2002/0006597 A1 | 1/2002 | Andreiko et al. | |
| 2002/0192617 A1 | 12/2002 | Phan et al. | |
| 2003/0009252 A1 | 1/2003 | Pavlovskaia et al. | |
| 2003/0139834 A1 | 7/2003 | Nikolskiy et al. | |
| 2003/0190576 A1 | 10/2003 | Phan et al. | |
| 2003/0198911 A1* | 10/2003 | Knopp | A61C 7/00 433/6 |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2005/0233276 A1* | 10/2005 | Kopelman | A61C 7/08 433/3 |
| 2006/0188834 A1* | 8/2006 | Hilliard | A61C 7/02 433/24 |
| 2008/0020337 A1 | 1/2008 | Phan et al. | |
| 2013/0089828 A1 | 4/2013 | Borovinskih et al. | |
| 2014/0120490 A1 | 5/2014 | Borovinskih et al. | |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 15500777 | 8/1979 |
| JP | 55358191 A | 5/1978 |
| JP | H0428359 A | 1/1992 |
| JP | 08508174 | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (No Date Given).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (No Date Given).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL< http://astronomy. swin.edu.au/—pbourke/prolection/coords>.

Boyd et al., "Three Dimensional Diagnosis and Orthodontic Treatment of Complex Malocclusions With the lnvisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

(56) References Cited

OTHER PUBLICATIONS

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at< http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, a Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 the Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (No Date Given).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (No Date Given).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.

(56) References Cited

OTHER PUBLICATIONS

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984).

KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventors CAD/CAM May Transform Dentistry," Dentist, 3 pages total, Sep. 1990.

Ponitz, "Invisible Retainers," Am. J. Orthod., 59(3):266-272 (Mar. 1971).

PROCERA Research Projects, "PROCERA Research Projects 1993—Abstract Collection," pp. 3-7; 28 (1993).

Proffit et al., Contemporary Orthodontics, (Second Ed.), Chapter 15, Mosby Inc., pp. 470-533 (Oct. 1993.

Raintree Essix & ARS Materials, Inc., Raintree Essix, Technical Magazine Table of contents and Essix Appliances,< http:// www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art'?", J. Amer. Dent. Assoc., 122:43-48 1991.

Rekow et a/., "CAD/CAM for Dental Restorations—Some of the Curious Challenges," IEEE Trans. Biomed. Eng., 38(4):344-345 (Apr. 1991.

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording the Dental Cast in Three Dimensions," Am. J. Orthod. Dentofacial Orthop., 92(3):199-206 (Sep. 1987).

Rudge, "Dental Arch Analysis: Arch Form, a Review of the Literature," Eur. J. Orthod., 3(4):279-284 1981.

Sakuda et al., "Integrated Information-Processing System in Clinical Orthodontics: An Approach with Use of a Computer Network System," Am. J. Orthod. Dentofacial Orthop., 101(3): 210-220 (Mar. 1992).

Schellhas et al., "Three-Dimensional Computed Tomography in Maxillofacial Surgical Planning," Arch. Otolamp!. Head Neck Sur9., 114:438-442 (Apr. 1988).

Schroeder et al., Eds. The Visual Toolkit, Prentice Hall PTR, New Jersey (1998) Chapters 6, 8 & 9, (pp. 153-210,309-354, and 355-428, respectively.

Shilliday, (1971). Minimizing finishing problems with the minipositioner, Am. J. Orthod. 59:596-599.

Siemens, "CEREC—Computer-Reconstruction," High Tech in der Zahnmedizin, 14 pages total (No Date Given).

Sinclair, "The Readers' Corner," J. Clin. Orthod., 26(6):369-372 (Jun. 1992).

Sirona Dental Systems GmbH, CEREC 3D, Manuel utiiisateur, Version 2.0X (in French), 2003,114 pages total.

Stoll et al., "Computer-aided Technologies in Dentistry," (article summary in English, article in German), Dtsch Zahna'rztl Z 45, pp. 314-322 (1990).

Sturman, "Interactive Keyframe Animation of 3-D Articulated Models," Proceedings Graphics Interface '84, May-Jun. 1984, pp. 35-40.

The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).

The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).

The Choice Is Clear: Red, White & Blue . . . The Simple, Affordable, No-Braces Treatment, Allesee Orthodontic Appliances-Pro Lab product information, 6 pages (2003).

(56) References Cited

OTHER PUBLICATIONS

The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (No Date Given).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pages (No Date Given).

* cited by examiner

AUTOMATIC PLACEMENT OF PRECISION CUTS

CROSS-REFERENCE

This application is a divisional application of U.S. application Ser. No. 14/148,453, filed Jan. 6, 2014, now U.S. Pat. No. 9,433,477, issued Sep. 6, 2016, which is a divisional application of U.S. application Ser. No. 13/270,171, filed Oct. 10, 2011, now U.S. Pat. No. 8,641,414, issued Feb. 4, 2014, each of which are incorporated herein by reference in their entirety, and to which applications we claim priority under 35 USC § 121.

BACKGROUND OF THE INVENTION

The present invention generally relates to the field of orthodontics, and more particularly to the design of dental positioning appliances precisely configured to interface with an orthodontic elastic member.

An objective of orthodontics is to move a patient's teeth to positions where function and/or aesthetics are optimized. Traditionally, appliances such as braces are applied to a patient's teeth by a treating practitioner and the set of braces exerts continual force on the teeth and gradually urges them toward their intended positions. Over time and with a series of clinical visits and adjustments to the braces, the practitioner adjusts the appliances to move the teeth toward their final destination.

More recently, alternatives to conventional orthodontic treatment with traditional affixed appliances (e.g., braces) have become available. For example, systems including a series of preformed appliances/aligners have become commercially available from Align Technology, Inc., Santa Clara, Calif., under the trade name Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "www-.invisalign.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as Treat™ software from Align Technology, Inc. The design of the aligners can rely on computer modeling of a series of planned successive tooth arrangements, and the individual aligners are designed to be worn over the teeth and elastically reposition the teeth to each of the planned tooth arrangements.

While recently developed orthodontic treatment technologies, such as those described above, represent a considerable advancement in the field of orthodontics, additional advancements remain of interest. For example, in some instances it may be advantageous to use an orthodontic elastic member to generate a tension force between a patient's upper and lower teeth to bring the teeth and/or jaws into a desired occlusion. In some traditional approaches, brackets are bonded to teeth in the upper and lower jaws and an orthodontic elastic member is used to couple the brackets to generate the tension force. Generating such a tension force in conjunction with recently developed orthodontic approaches can be challenging. For example, shell aligners are often designed to match the geometry of a patient's teeth, thereby leaving little room for bonding such brackets to a patient's teeth. In some cases, dental practitioners are left with the daunting task of trimming or otherwise self-manipulating shell aligners to receive orthodontic elastic members such as elastic bands and/or adapt to existing orthodontic appliances such as brackets already disposed on the patient's teeth. As such, there is a need for shell aligners that can be used in conjunction with an orthodontic elastic member to, for example, bring a patient's teeth into a desired occlusion.

SUMMARY OF THE INVENTION

The present disclosure provides orthodontic positioning appliances for use with an orthodontic elastic band, and related systems and methods. The disclosed methods and systems include methods and systems for designing a patient removable orthodontic positioning device for use with an orthodontic elastic band. The orthodontic positioning device includes a first patient removable orthodontic tooth positioning appliance having teeth receiving cavities shaped to receive and apply a resilient positioning force to a patient's teeth provided in one of an upper jaw and a lower jaw. The first appliance includes a hook configured to receive an orthodontic elastic band. The orthodontic positioning device also includes a second patient removable orthodontic tooth positioning appliance having teeth receiving cavities shaped to receive and apply a resilient positioning force to a patient's teeth provided in the other of the upper jaw and the lower jaw. The second appliance includes a cutout operable to expose an orthodontic elastic band receiving member.

For a fuller understanding of the nature and advantages of the present invention, reference should be made to the ensuing detailed description and accompanying drawings. Other aspects, objects and advantages of the invention will be apparent from the drawings and detailed description that follows.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
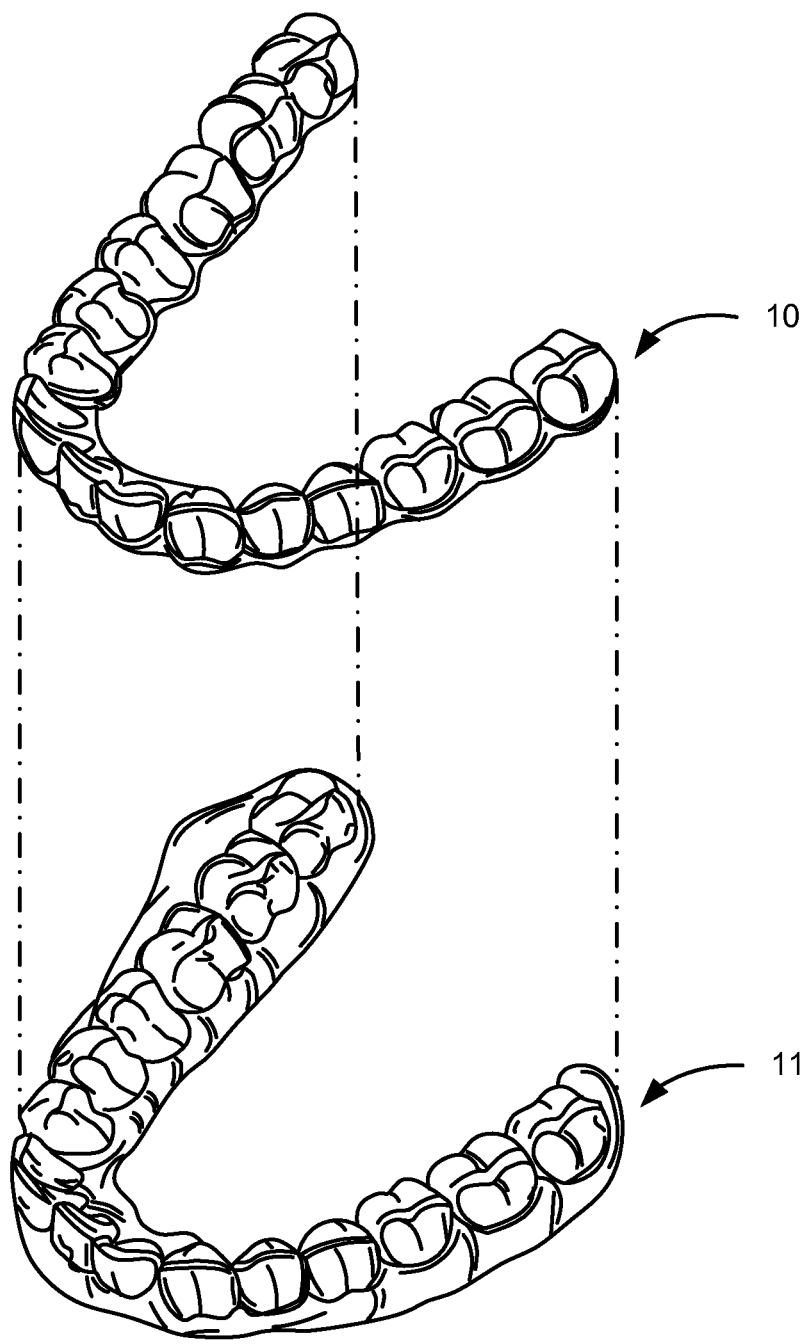
FIG. 1 illustrates a jaw and an incremental positioning appliance for the jaw, in accordance to an embodiment.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Orthodontic positioning appliances are provided that can be used in conjunction with one or more orthodontic elastic members, as well as related methods and systems. During orthodontic treatment, it may be necessary to apply forces to a tooth to generate movement of the tooth to, for example, bring the patient's teeth into a better occlusion in a mesial or distal direction. The presently disclosed appliances, methods, and systems provide means by which such forces can be applied during orthodontic treatment where appliances having teeth receiving cavities are used, such as preformed appliances/aligners available from Align Technology, Inc., Santa Clara, Calif., under the trade name Invisalign® System, and where a patient has an elastic band receiving member (e.g., an orthodontic button or a bracket with a hook) affixed to one or more of their teeth.

In one embodiment, orthodontic positioning appliances may include a first appliance for coupling to a patient's teeth in one jaw (e.g., the upper jaw), and a second appliance for coupling to patient's teeth in another jaw (e.g., the lower jaw). The patient may have an elastic band receiving member (e.g., an orthodontic button) affixed to one of their teeth, such as a molar in the lower jaw. The second appliance may then be designed and fabricated to include a cutout operable to expose the elastic band receiving member or otherwise prevent physical and/or functional interference with the elastic band receiving member. Further, the first appliance may include a cutout defining a hook, such as a hook provided on an incisor of a tooth in the lower jaw. As a result, an elastic band may be attached to the hook of the first appliance and the elastic band receiving member affixed to the molar, thereby advantageously using existing orthodontic elements (such as the orthodontic button) and new appliances, as well as advantageously using the new appliances to apply forces via both their teeth receiving cavities and via the existing orthodontic elements.

Embodiments also include methods for designing patient removable orthodontic tooth positioning appliances including cutouts. In one embodiment, computer-based 3-dimensional planning/design tools, such as Treat™ software from Align Technology, Inc., may be used to design and fabricate a tooth positioning appliance including a cutout to expose an elastic band receiving member. A digital representation of a patient's tooth or teeth may initially be received. A treating practitioner may then select a digital representation of the elastic band receiving member, and place the digital representation of the elastic band receiving member on the digital representation of the patients tooth. The digital representation of the elastic band receiving member may initially be provided in a default location defined by the computer-based planning/design tools, and may subsequently be modified by the treating practitioner. In some embodiments, conditions may be imposed to restrict a location of the digital representation of the elastic band receiving member. Once the digital representation of the elastic band receiving member is provided on the digital representation of the patients tooth, the computer-based planning/design tools may define a cutout line. The cutout line may subsequently be used to cut the tooth positioning appliance such that the appliance does not interfere with the elastic band receiving member when disposed on the patient's teeth. In some embodiments, the cutout line may have be optimally shaped so as to minimize the amount of material removed from the tooth positioning appliance. In at least one embodiment, the cutout line may be user-manipulable such that the treating practitioner may redefine a location and/or shape of the cutout line.

Embodiments also include methods for designing patient removable orthodontic tooth positioning appliances including hooks. In one embodiment, computer-based 3-dimensional planning/design tools may be used to design and fabricate a tooth positioning appliance including a hook operable to couple to an elastic band. A digital representation of a patient's tooth or teeth may initially be received. A treating practitioner may then generate a hook cutout line extending from the gingival line of a tooth. The hook cutout line may initially be provided in a default location defined by the computer-based planning/design tools, and may subsequently be modified by the treating practitioner. In some embodiments, conditions may be imposed to restrict a location of the hook cutout line. Once the hook cutout line is provided on the digital representation of the patients tooth, the computer-based planning/design tools may extend the hook cutout line. The extended hook cutout line may subsequently be used to cut the tooth positioning appliance such that the appliance is operable to receive an elastic band when disposed on the patient's teeth. In some embodiments, the hook cutout line may have be optimally shaped so as to extend in a direction toward a center of an elastic band receiving member affixed to a patient's tooth. In at least one embodiment, the hook cutout line may be user-manipulable such that the treating practitioner may redefine a location and/or shape of the cutout line.

In some embodiments, a method of detecting a malocclusion of a patient's teeth is provided. In detecting malocclusion, the method may detect various types of malocclusion, such as Class I type malocclusion (neutrocclusion), Class II type malocclusion (distocclusion), and/or Class III type malocclusion (mesiocclusion). According to one embodiment, to detect a malocclusion of a patient's teeth, the computer-based planning/design tools may receive a digital representation of the patient's teeth in both the upper jaw and the lower jaw. The digital representations of the teeth in the jaws may be aligned in accordance with the patient's natural occlusion. Points on corresponding teeth in the upper and lower jaws (e.g., center points of canine teeth) may be identified, a distance there between measured. Based on the measured distance, a type of malocclusion (such as distocclusion or mesiocclusion) may be determined.

Referring now to the drawings, in which like reference numerals represent like parts throughout the several views, FIG. 1 provides an appropriate starting point in a detailed discussion of various embodiments of the present invention with respect to tooth repositioning appliances designed to apply repositioning forces to teeth. A tooth repositioning appliance 10 can be worn by a patient in order to achieve an incremental repositioning of individual teeth in the jaw 11. The appliance can include a shell (e.g., a polymeric shell) having teeth-receiving cavities that receive and resiliently reposition the teeth. In many embodiments, a polymeric appliance can be formed from a thin sheet of suitable elastomeric polymeric material, such as a 0.03 inch thermal forming dental material by Tru-Tain Plastics, Rochester, Minn. An appliance can fit over all teeth present in an upper or lower jaw, or less than all of the teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "www-.invisalign.com").

An appliance can be designed and/or provided as part of a set or plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include where surgery is recommended, where inter-proximal reduction (IPR) is appropriate, where a progress check is scheduled, where anchor placement is best, where palatal expansion is desirable, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages. The adjustment appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

During a course of orthodontic treatment, it may be desirable to interface patient-removable tooth positioning appliances with orthodontic members that are affixed to a surface (e.g., a lingual or buccal surface) of a patient's teeth. For example, it may be desirable to interface patient-removable tooth positioning appliances with an orthodontic member that is operable to receive an elastic band, such as an orthodontic button. The patient-removable tooth positioning appliances may then be coupleable to the elastic band so that tooth repositioning forces may be applied by the elastic band between the orthodontic button and the patient-removable tooth positioning appliances.

Figure 2:
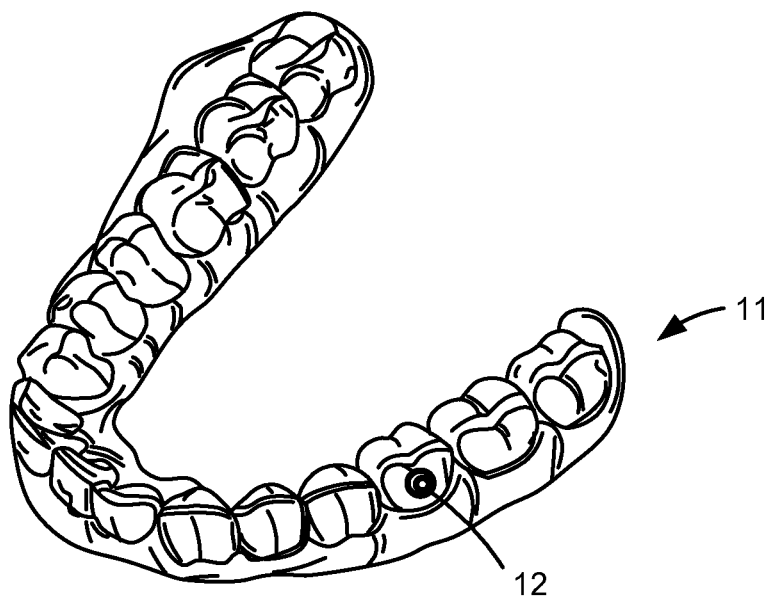
FIG. 2 illustrates a jaw including an elastic band receiving member.

FIG. 2 illustrates a jaw 11 including an elastic band receiving member 12. Elastic band receiving member 12 may be any orthodontic appliance affixed to a patient's tooth operable to receive a force generating element such as an elastic band. For example, the elastic band may wrap around at least a portion of elastic band receiving member 12 and, when in tension, apply a force to the tooth which elastic band receiving member 12 is affixed to and/or the jaw which the tooth is a part of.

While shown as being disposed on a buccal surface of a tooth in the lower jaw, elastic band receiving member 12 may be attached to any suitable surface of any suitable tooth of any suitable jaw. For example, elastic band receiving member 12 may be attached to a tooth surface including a facial surface, lingual surface, palatal surface, etc., may be attached to a tooth including a wisdom tooth, a molar, a bicuspid, etc., and may be attached to a tooth in either the upper or lower jaw of the patient.

In some embodiments, elastic band receiving member 12 may be an orthodontic button. However, elastic band receiving member 12 may assume any suitable shape for attaching to a surface of a patient's tooth and receiving a force generating element such as an elastic band. Elastic band receiving member 12 may be operable not only to receive a force generating element such as an elastic band, but may also be operable to perform one or more additional functions. For example, elastic band receiving member 12 may be an orthodontic bracket including a hook, accordingly being operable to both receive an orthodontic wire and an orthodontic elastic band.

In other embodiments, elastic band receiving member 12 may be a temporary anchorage device (TAD) provided in the patient's mouth at a location other than an exposed surface of the patient's teeth. For example, elastic band receiving member 12 may be a retraction screw inserted through the gingival tissue and embedded into a bone of the patient's mouth. The TAD may be embedded into any suitable bone at any suitable location in the patient's mouth. For example, the TAD may be embedded into bone at a location between the second premolar and the first molar, or between the first and second molars. The TAD may be embedded into bone from any suitable surface of the mouth, including either buccal or lingual facing bone surfaces.

Figure 3:
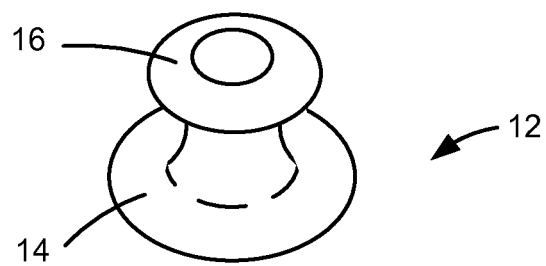
FIG. 3 illustrates an elastic band receiving member according to one embodiment.

FIG. 3 illustrates an elastic band receiving member 12 according to one embodiment. In this embodiment, elastic band receiving member 12 is an orthodontic button. Elastic band receiving member 12 includes a base 14 for bonding elastic band receiving member 12 to a patient's tooth. The surface of base 14 to be bonded to the patient's tooth may have any suitable shape. The shape shown in FIG. 3 is circular, however the shape may alternatively be oval, square, rectangular, polygonal, or any other suitable shape for bonding to a surface of a patient's tooth.

Elastic band receiving member also includes a band-receiving portion 16. Band-receiving portion 16 extends from base 14 and is shaped to receive a force generating element such as an elastic band. Band-receiving portion 16 may have any suitable shape for receiving the force generating element, such as hook-shaped, mushroom-shaped, shaped to include a ball provided on an end surface of a column, etc.

According to various embodiments, it is desirable to shape a patient-removable orthodontic tooth positioning appliance such that the tooth positioning appliance does not interfere with elastic band receiving member 12. In this fashion, not only may the patient-removable orthodontic tooth positioning appliance be operable to apply tooth positioning or re-positioning forces by way of its tooth receiving cavities, but also elastic band receiving member 12 may be engaged to also apply tooth/jaw positioning or re-positioning forces.

In engaging with elastic band receiving member 12, it may be desirable to use an additional elastic band receiving member disposed on a tooth in a jaw opposite the jaw which elastic band receiving member 12 is located. However, in doing so, the additional elastic band receiving member may need to be provided in an undesirable location, such as on a facial surface of a canine tooth. Accordingly, it may instead be desirable to use a patient-removable orthodontic tooth positioning appliance rather than an additional elastic band receiving member to engage the elastic band. In this case, a patient-removable orthodontic tooth positioning appliance provided for one jaw (such as the upper jaw) may be adapted to receive the elastic band (e.g., the appliance may include a hook), while a patient-removable orthodontic tooth positioning appliance provided for the other jaw (such as the lower jaw) may be adapted to avoid interference with an elastic band receiving member disposed on a tooth (e.g., a button on a tooth of the lower jaw). The pair of patient-removable orthodontic tooth positioning appliances may then be operable to apply tooth positioning or repositioning forces in accordance with their tooth receiving cavities, and may be operable to allow an orthodontic elastic band to be coupled between a hook of one appliance and a button disposed on a tooth so as to provide further tooth/jaw positioning/repositioning forces.

Figure 4A:
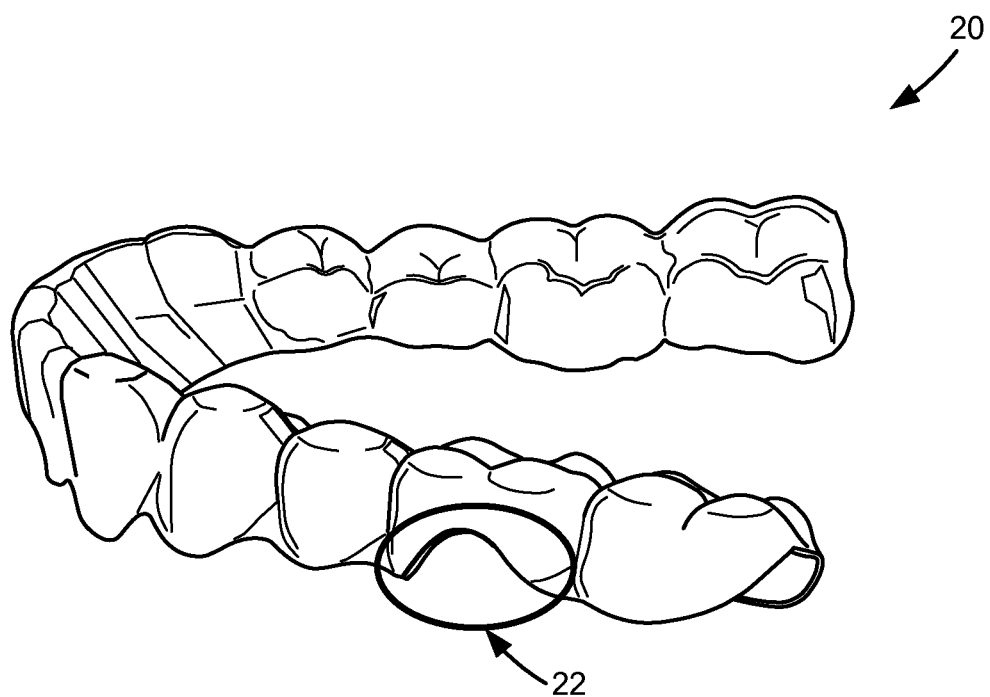
FIG. 4A illustrates a patient-removable tooth positioning appliance including a cutout.

FIG. 4A illustrates a patient-removable tooth positioning appliance 20 similar to appliance 10 discussed with reference to FIG. 1. However, in this case, tooth positioning appliance 20 includes a cutout 22. Cutout 22 is shaped to avoid physical and/or functional interference with an elastic band receiving member such as elastic band receiving member 12 discussed with reference to FIG. 2 and FIG. 3. For example, cutout 22 may have a parabolic or otherwise curved shape, where cutout 22 protrudes into a gingival-facing surface of tooth positioning appliance 20 a distance at least halfway between the gingival line (of a patient's tooth when tooth positioning appliance 20 is attached to the teeth) and an occlusal surface of the tooth.

While shown as being adjacent to a buccal surface of a tooth in the lower jaw (when tooth positioning appliance 20 is attached to the teeth), cutout 22, similar to elastic band receiving member 12, may be provided on any suitable surface of any suitable tooth receiving cavity of a patient-removable tooth positioning appliance 20 designed for any suitable jaw. In some embodiments, cutout 22 is provided for a tooth surface on which an elastic band receiving member 12 is disposed for a given treatment period. However, in other embodiments, cutout 22 may provide for a tooth surface on which an elastic band receiving member 12 is not disposed for a given treatment period. For example, elastic band receiving member 12 may be planned to be used in a future treatment period, or may have previously been used during a past treatment period.

Figure 4B:
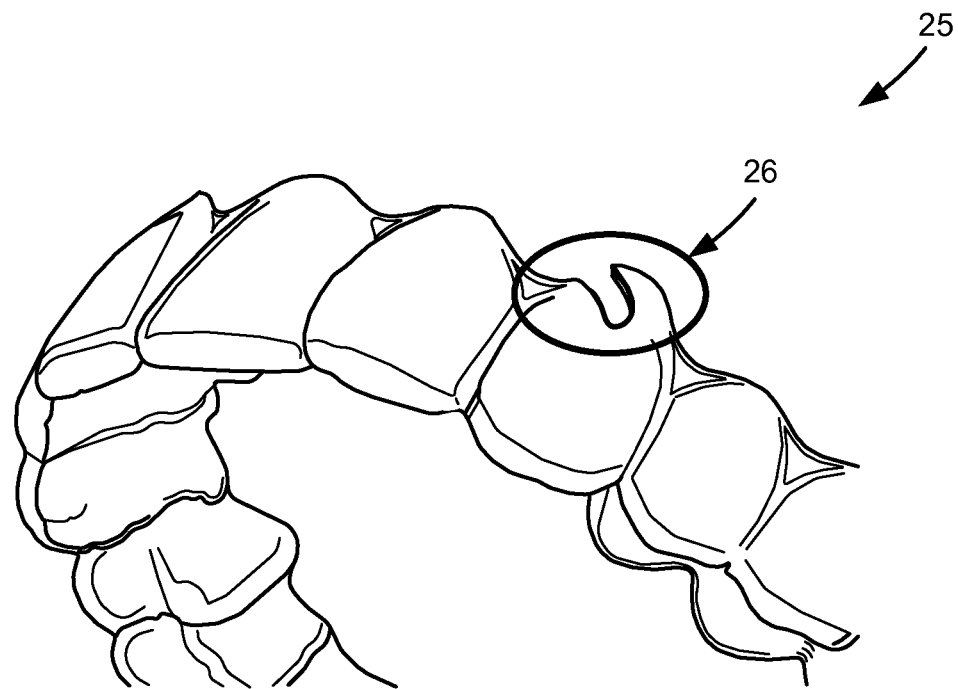
FIG. 4B illustrates a patient-removable tooth positioning appliance including a hook.

FIG. 4B illustrates a patient-removable tooth positioning appliance 25 similar to appliance 10 discussed with reference to FIG. 1. However, in this case, tooth positioning appliance 20 includes a hook 26, where hook is operable to receive an elastic band. In the embodiment shown in FIG. 4B, hook 26 is formed by cutting out a portion of tooth positioning appliance 25 and protruding along a gingival-facing surface of tooth positioning appliance 25. However, hook 26 may have any suitable shape for receiving an elastic band, including any of those discussed in U.S. patent application Ser. No. 12/722,130, entitled "REINFORCED ALIGNER HOOKS", which is commonly assigned and incorporated by reference herein in its entirety for all purposes.

While shown as being adjacent to a facial surface of a tooth in the upper jaw (when tooth positioning appliance 25 is attached to the teeth), hook 26, similar to cutout 22 discussed with reference to FIG. 4A, may be provided on any suitable surface of any suitable tooth receiving cavity of a patient-removable tooth positioning appliance 20 designed for any suitable jaw. In some embodiments, hook 26 is provided on the same tooth surface (although for a different tooth) for which cutout 22 is provided. However, in other embodiments, hook 26 may provided for a tooth surface different than that which cutout 22 is provided.

In some embodiments, a patient-removable tooth positioning appliance having cutout 22 may be provided for disposal on a patient's teeth at the same time at which a patient-removable tooth positioning appliance having hook 26 may be provided for disposal on the patient's teeth. Cutout 22 and hook 26 may be provided for different teeth on different jaws so that coupling of an orthodontic elastic band may operate to apply tooth/jaw repositioning forces sufficient to treat tooth malocclusions such as distocclusion or mesiocclusion. For example, cutout 22 may be provided for disposal over a posterior tooth in one jaw, while hook 26 may be provided for disposal over an anterior tooth in another jaw. In this fashion, an orthodontic elastic band may operate to apply tooth/jaw repositioning forces that tend to move one or more teeth or the jaw in a mesial or distal direction.

In one embodiment, the present invention can include an orthodontic treatment system including one or more sets of aligners utilizing elastics. An exemplary set of aligners is described with reference to FIGS. 5A and 5B, where the set includes a first aligner for a first dental arch of a patient and a second aligner for a second dental arch of the patient. One aligner of the set may include a hook adapted to receive an elastic, and the other aligner can include an receiving member or cutout to accommodate a receiving member. In such a set, the aligners of the set can be configured to accommodate an elastic coupling the hook and receiving member. A treatment system can include one or more sets of aligners according to systems described herein.

Figure 5A:
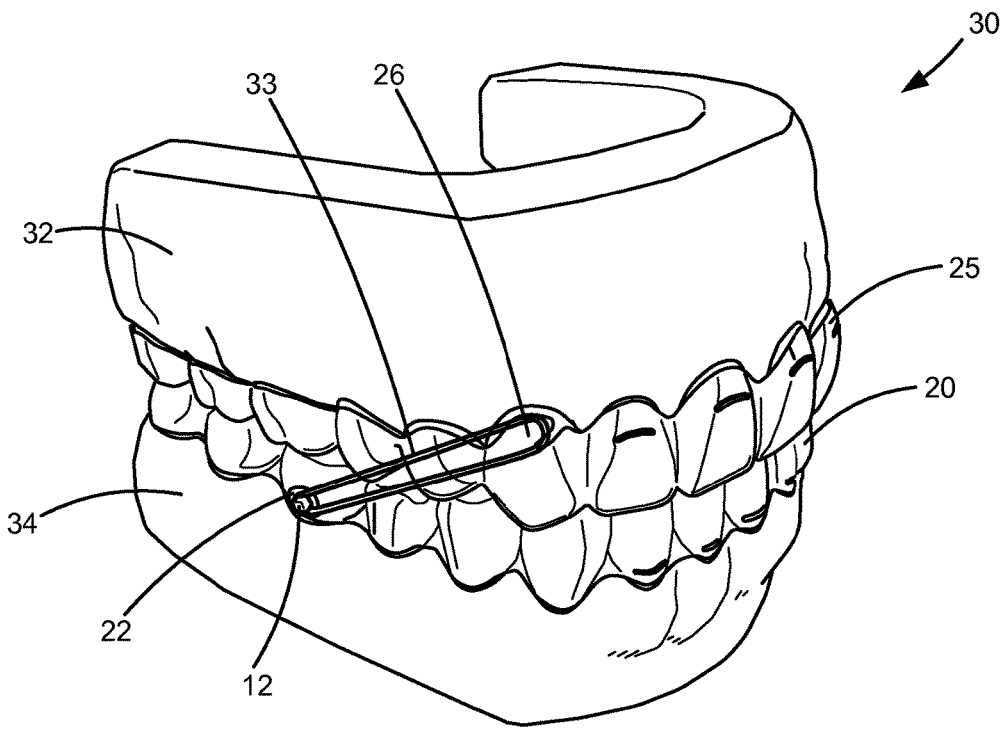
FIG. 5A is an isometric view of an orthodontic positioning device according to an embodiment.

FIG. 5A is an isometric view of an orthodontic positioning device 30 according to an embodiment. Orthodontic positioning device 30 includes a first patient removable orthodontic tooth positioning appliance 25 having teeth receiving cavities shaped to receive and apply a resilient positioning force to a patient's teeth provided in an upper jaw 32 of the patient. Tooth positioning appliance 25 includes hook 26 adapted to receive elastic band 33. Orthodontic positioning device 30 also includes a second patient removable orthodontic tooth positioning appliance 20 having teeth receiving cavities shaped to receive and apply a resilient positioning force to a patient's teeth provided in a lower jaw 34 of the patient. Tooth positioning appliance 20 includes cutout 22 shaped to avoid physical and/or functional interference with elastic band receiving member 12. Orthodontic positioning device 30, in some embodiments, may also include elastic band 33 and/or elastic band receiving member 12.

In the embodiment shown in FIG. 5A, hook 26 is disposed over a facial surface of the patient's canine tooth provided on the right side of the upper jaw, while cutout 22 is disposed over elastic band receiving member 12 that is coupled to a facial surface of the patient's first molar provided on the right side of the lower jaw. However, as previously discussed, hook 26 and cutout 22 may be provided over any suitable teeth. In the embodiment shown in FIG. 5A, elastic band 33 is coupled between hook 26 and elastic band receiving member 12 and may be operable to apply a tooth/jaw positioning/repositioning forces in the mesial or distal directions.

Figure 5B:
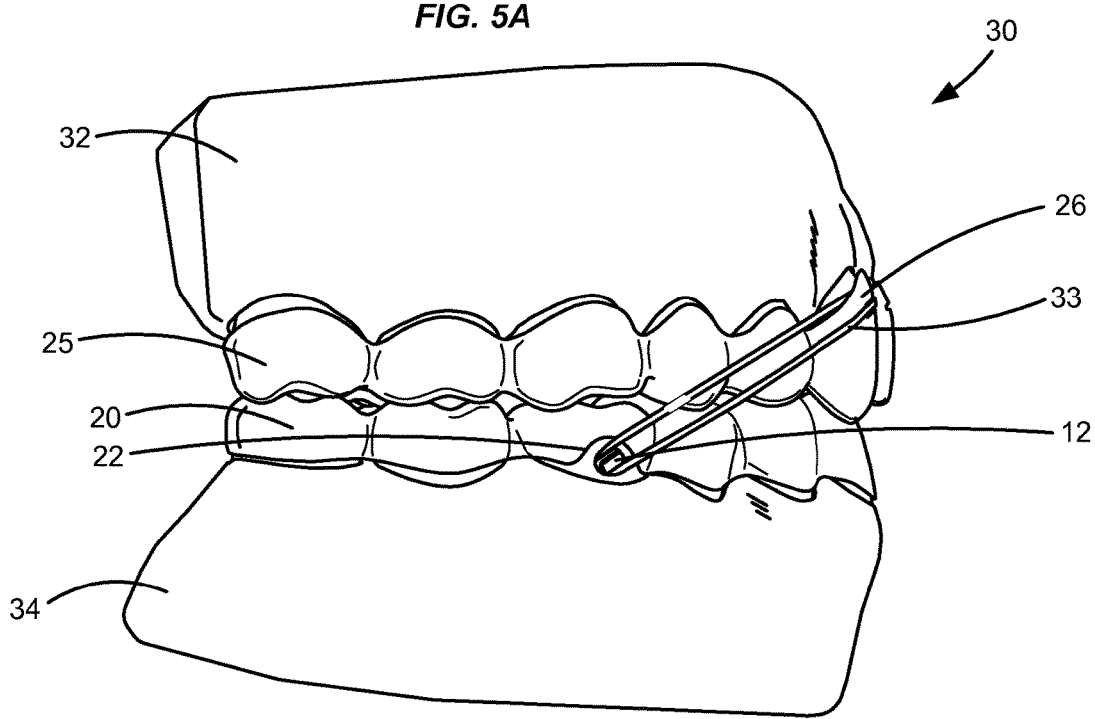
FIG. 5B is a side view of the orthodontic positioning device of FIG. 5A.

FIG. 5B is a side view of the orthodontic positioning device of FIG. 5A. As shown in FIG. 5B, cutout 22 may be shaped to avoid physical and/or functional interference with elastic band receiving member 12. Further, hook 26 may be shaped to follow a contour of the patient's teeth and/or may have a facial surface that is substantially parallel with and/or does not extend (in a facial direction) past other portions of the tooth receiving cavity in which hook 26 is provided. In other words, with reference to the orientation shown in FIG. 5B, hook 26 does not protrude horizontally in a direction away from other portions of patient-removable tooth positioning appliance 25, thereby reducing undesirable contact or interference with the tissue on an inner surface of a patient's mouth.

In some embodiments, methods for treating dental malocclusions are provided. In such embodiments, dental malocclusions may be detected using digital representations (such as 3-dimensional models) of a patient's tooth arrangement, including digital representations of teeth in the patient's upper jaw, and digital representations of teeth in the patient's lower jaw. If a malocclusion is detected, computer-based 3-dimensional planning/design tools, such as Treat™ software from Align Technology, Inc., may be used to design and subsequently fabricate tooth positioning appliances including cutouts and hooks. The cutouts may be designed by digitally simulating the placement of elastic band receiving members such as orthodontic buttons and defining appliance cutout lines around portions of the buttons so that a resulting tooth positioning appliance does not interfere with the actual button attached to the patient's tooth. The hook may be designed by digitally placing, sizing, and orienting a hook, where an orientation of the hook may be optimized based on a location of a cutout in another tooth positioning appliance or a location of a corresponding elastic band receiving member.

Figure 6:
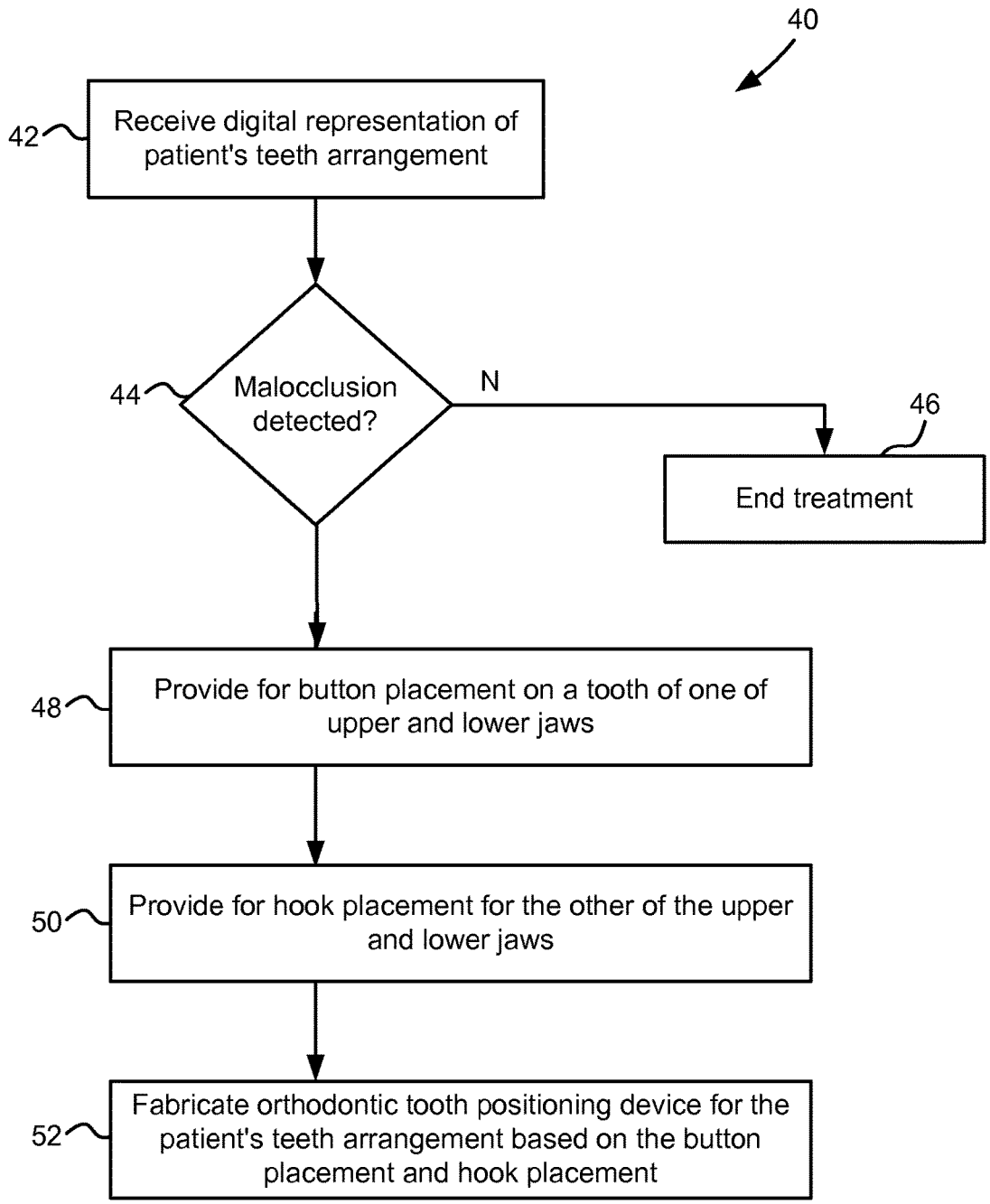
FIG. 6 is a simplified block diagram illustrating a method for treating dental malocclusions.

FIG. 6 is a simplified block diagram illustrating a method 40 for treating dental malocclusions. In operation 42, digital representations of a patient's teeth arrangement are received. The digital representations may include a 3-D model of the patient's teeth including tooth crowns provided in the upper and/or lower jaws, where the digital representations of the teeth may be segmented or unsegmented. The digital representations may also include gingiva and/or other dental features provided in proximity to the patient's teeth. The digital representations may be received in any suitable manner. For example, the patient's teeth may be scanned using one or more imaging devices suitable to generate 3-D models of the teeth. In one embodiment, the digital representations may be manipulated to represent the teeth in an arrangement other than a current teeth arrangement of the patient. For example, the digital representations may be manipulated to represent the patient's teeth in a desired intermediate or final position.

In operation 44, a determination is made as to whether malocclusions are detected. In detecting a malocclusion, the digital representations of the patient's teeth provided in the upper and lower jaws may be used. Malocclusion may be a Class I type malocclusion, i.e., neutrocclusion, whereby the buccal teeth have a correct mesiodistal relationship with respect to one another, but other teeth may have other types of positioning problems such as overcrowding. Malocclusion may be a Class II type malocclusion, i.e., distocclusion, whereby the lower teeth are in a distal position compared to the upper teeth. Or malocclusion may be a Class III type malocclusion, i.e., mesiocclusion, in which the lower teeth are positioned mesially compared to the upper teeth.

If a Class I type malocclusion is detected, treatment may end in accordance with operation 46. On the other hand, if a Class II type malocclusion or a Class III type malocclusion are detected, treatment may continue with operation 48. In operation 48, a digital representation of an orthodontic button may be placed on a digital representation of a tooth of one of the upper and lower jaws. The digital representation of the orthodontic button may be, for example, a digital representation of the previously discussed elastic band receiving member 12. Like elastic band receiving member 12, the orthodontic button may be placed on any suitable surface of any suitable tooth of any suitable jaw. In one embodiment, the digital representation of the orthodontic button is placed on the same tooth and in the same orientation and position which elastic band receiving member 12 is provided.

In operation 50, a hook placement may be provided for a tooth of one of the upper and lower jaws. The hook placement may be defined with reference to a digital representation of a patient's tooth, and may itself define a shape of a hook to be subsequently formed in a tooth positioning appliance. For example, the hook placement may define a shape of the previously discussed hook 26. Like hook 26, the hook placement be defined for any suitable surface of any suitable tooth of any suitable jaw.

In operation 52, an orthodontic positioning device is fabricated for the patient's teeth arrangement based on the digital representation of the orthodontic button and the hook placement. The orthodontic positioning device may include a first patient removable orthodontic tooth positioning appliance such as patient removable orthodontic tooth positioning appliance 20 discussed with reference to FIG. 5A, and may include a second patient removable orthodontic tooth positioning appliance such as patient removable orthodontic tooth positioning appliance 25 discussed with reference to FIG. 5B. In fabricating patient removable orthodontic tooth positioning appliance 20, the digital representation of the orthodontic button may be used to form cutout 22 so that patient removable orthodontic tooth positioning appliance 20 does not interfere with elastic band receiving member 12. In fabricating patient removable orthodontic tooth positioning appliance 25, the hook placement may be used to form hook 26.

It should be appreciated that method 40 may be implemented by any suitable electronic computing device, server, or system. A system that may be used in accordance with one embodiment is discussed later with reference to FIG. 18. Further, the specific operations illustrated in FIG. 6 provide a particular method of treating dental malocclusions, according to certain embodiments of the present invention. Other sequences of operations may also be performed according to alternative embodiments. For example, alternative embodiments of the present invention may perform the operations outlined above in a different order. Moreover, the individual operations illustrated in FIG. 6 may include multiple sub-operations that may be performed in various sequences as appropriate to the individual operations. Furthermore, additional operations may be added or existing operations removed depending on the particular applications. One of ordinary skill in the art would recognize and appreciate many variations, modifications, and alternatives.

In some embodiments, a type of malocclusion of the patient's teeth (e.g., Class I, II, or III) may be detected using any one of numerous techniques such as that discussed with reference to operation 44 of FIG. 6. In one particular technique, digital representations of the patient's teeth (both upper and lower jaw) may be used to detect a type of malocclusion. In using the digital representations of the patient's teeth, the teeth in the upper and lower jaws may be aligned in accordance with the patient's natural occlusion. Corresponding points on corresponding teeth in the upper and lower jaws may then be identified. For example, center points of facial surfaces of left canine teeth in the upper and lower jaws may be identified. A distance may then be calculated using these points, and based on the distance, a type of malocclusion detected.

Figure 7:
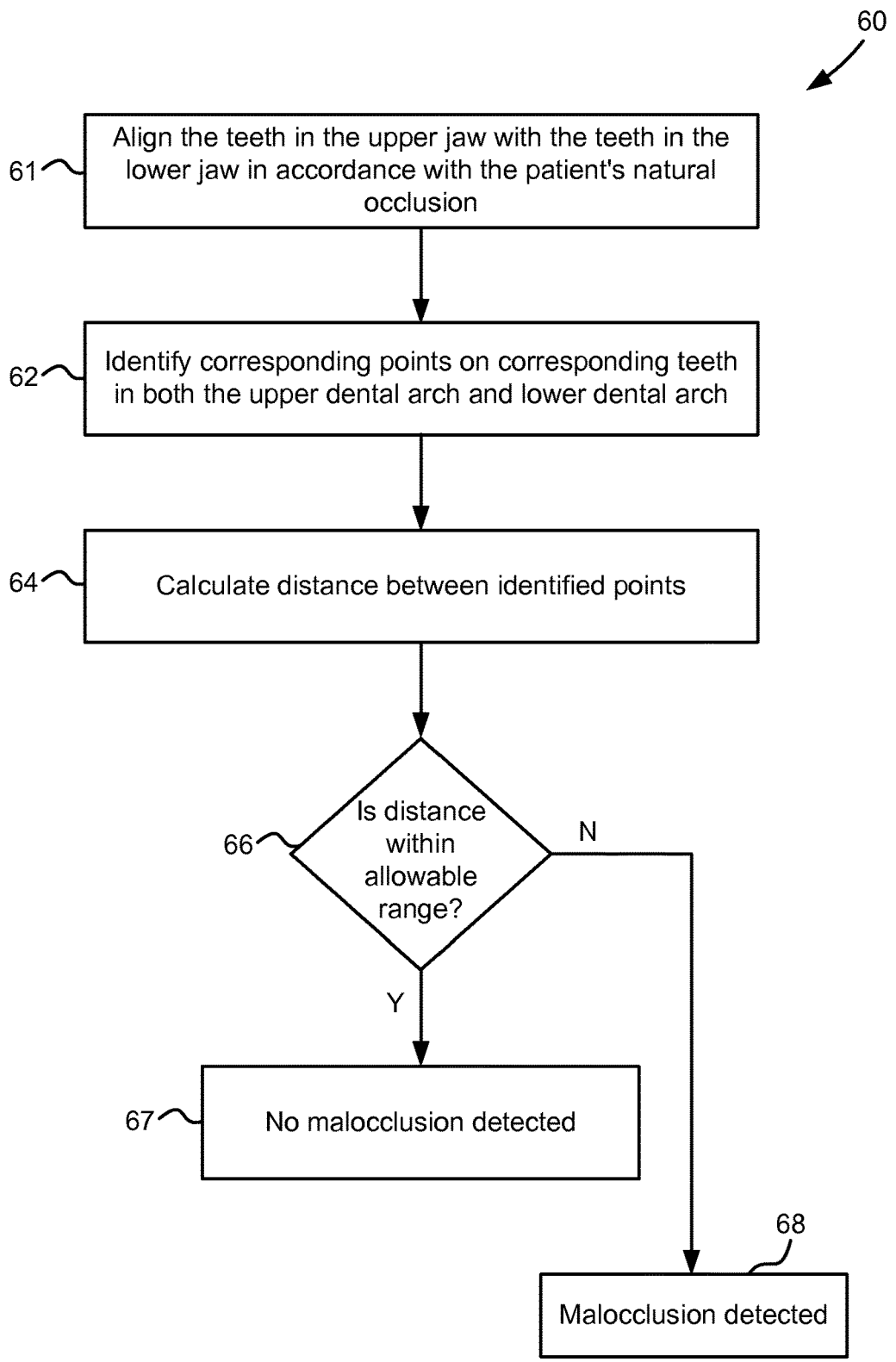
FIG. 7 is a simplified block diagram illustrating a method for detecting dental malocclusions.

FIG. 7 is a simplified block diagram illustrating a method 60 for detecting dental malocclusions. In one embodiment, the operations depicted and discussed with reference to method 60 may correspond to the malocclusion detection operation 44 discussed with reference to FIG. 6. Accordingly, a digital representation of a patient's teeth arrangement may initially be acquired, as discussed with reference to operation 42 of FIG. 6.

In operation 61, the teeth in the patient's upper jaw are aligned with the teeth in the patient's lower jaw in accordance with the patient's natural occlusion. For example, the digital representation of the teeth in the patient's upper jaw may be aligned with the digital representation of the teeth in the patient's lower jaw. Any one of a variety of techniques may be used to performing such a digital alignment. In one embodiment, the patient's teeth may scanned while they are in occlusion, and the subsequent image used as the image representing the aligned teeth. In another embodiment, the patient's teeth may be scanned while they are in occlusion, and subsequently used to align 3-D models of the patient's teeth using surface matching techniques or other suitable image matching techniques.

In operation 62, corresponding points on corresponding teeth in both an upper dental arch and a lower dental arch are identified. The teeth chosen may be any suitable teeth in the upper and lower dental arches. For example, the canine tooth on the right side of an upper jaw may be chosen, as well as the canine tooth on the right side of the lower jaw. Alternatively, other corresponding teeth may be chosen, such as incisors, premolars, or molars, on any suitable side, including the left or right side of the jaws. Further, a common point may be identified at any suitable location on the teeth. For example, the common point may be a center of the facial surface of the tooth crowns. For other examples, the common point may be at location on the facial surface of the teeth other than the center, such as a location near the gingival or near the occlusal surface of the teeth. For yet other examples, the common point may be at features of the teeth provided at locations other than the facial surface, and may include, for example, cusps, ridges, grooves, or other features that are common between the identified teeth.

Figure 8A:
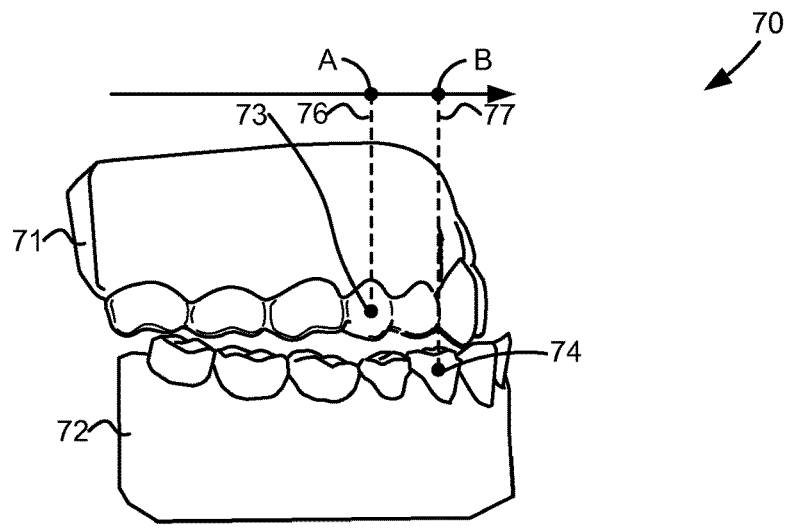
FIG. 8A shows a tooth arrangement with a Class II type malocclusion (distocclusion).
Figure 8B:
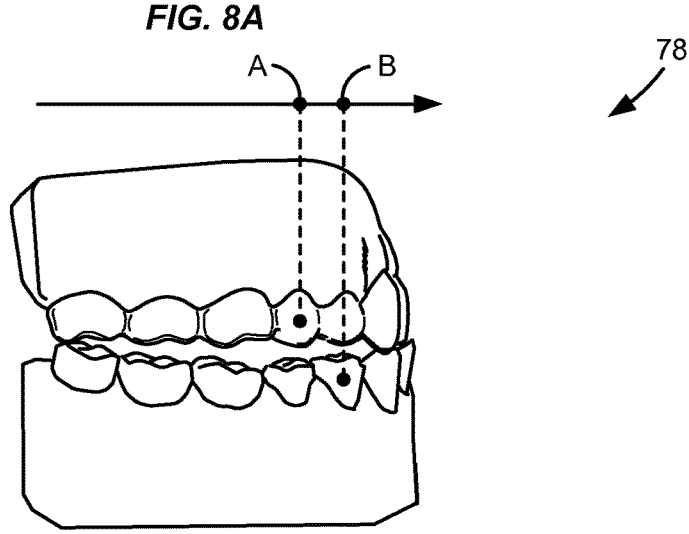
FIG. 8B shows a tooth arrangement with a Class I type malocclusion (neutrocclusion).
Figure 8C:
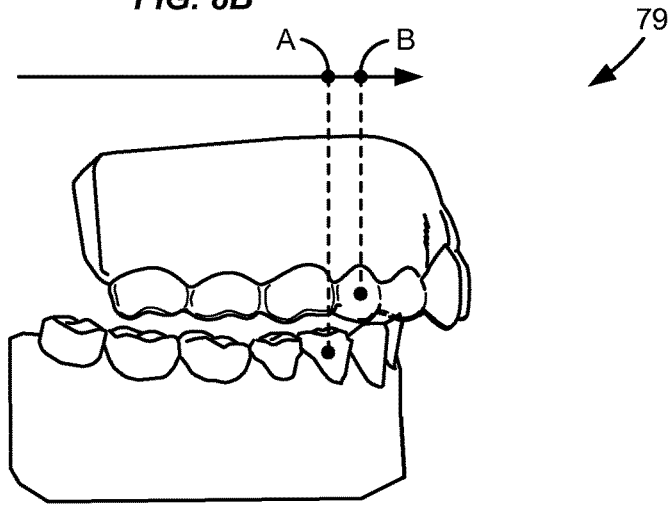
FIG. 8C shows a tooth arrangement with a Class III type malocclusion (mesiocclusion).

FIGS. 8A to 8C are simplified images of teeth arrangements having different malocclusion types that may aid in the discussion of methods for detecting dental malocclusions. FIG. 8A shows a tooth arrangement 70 including an upper jaw 71 and lower jaw 72. First point 73 is identified on the center of a facial surface of the right-side canine tooth in the upper jaw. Second point 74 is identified on the center of a facial surface of the right-side canine tooth in the lower jaw.

Turning back to FIG. 7, in operation 64, a distance between the identified points is calculated. The distance may be calculated in one or more of a variety of fashions. For example, a line may be drawn between the identified points, where the distance is calculated as the length of the line. For another example, lines may be drawn in parallel with one another from each identified point to a single plane. A distance along one axis of that plane, where the axis is arranged in the mesial/distal direction, may then be measured between the intersection points of the drawn lines and the plane. For instance, with reference to FIG. 8A and considering the orientation of the tooth arrangement 70 as illustrated, parallel lines 76 and 77 may be drawn extending from points 73 and 74. Lines 76 and 77 may be drawn in a direction perpendicular to the occlusal plane and terminate at a line extending in the mesial/distal direction. The distance may then be measured as the distance between the intersection points, i.e., between points A and B shown in FIG. 8A.

Figure 9A:
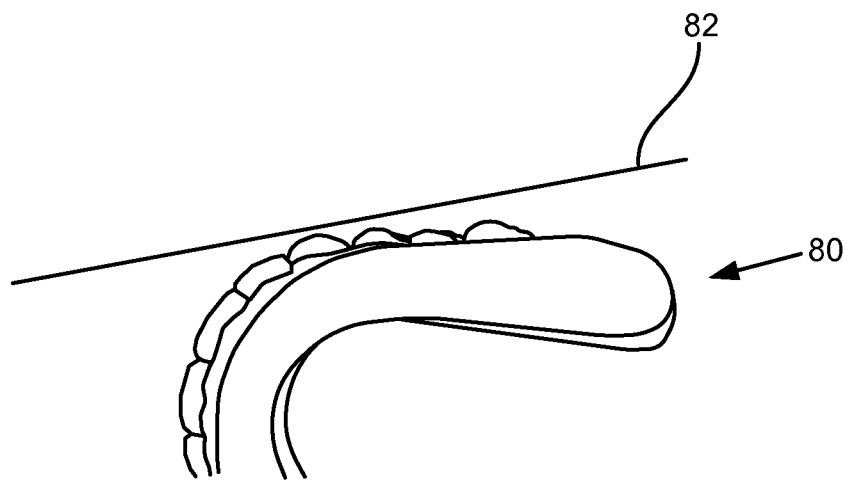
FIG. 9A is a top view of a tooth arrangement including a tangent line.

For yet another example, a distance may be calculated along a tangent direction. FIG. 9A is a top view of a tooth arrangement 80 including a tangent line 82. Tangent line 82 is representative of a tangent direction, and in this embodiment is calculated as the average direction between lines which are tangent to each of a tooth in the upper jaw and the lower jaw in the mesial-distal direction. In this embodiment, the teeth are canines of the upper and lower jaws.

Figure 9B:
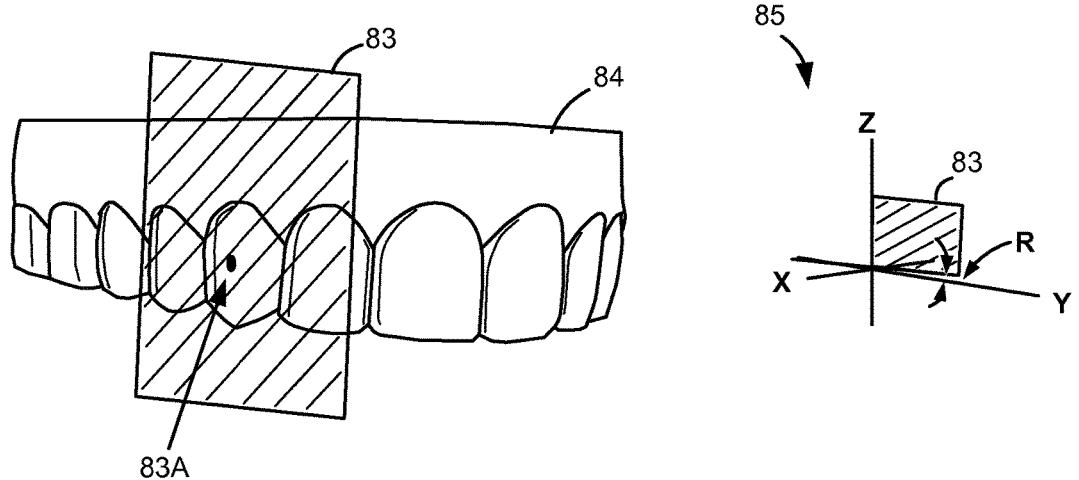
FIG. 9B shows a plane that is tangential to a point on a tooth of the upper jaw.

Numerous techniques may be used for determining tangent line 82. In one embodiment, tangential planes may be generated for points on each of a pair of corresponding teeth in the upper and lower jaws and subsequently used to determine tangent line 82. For example, with respect to a tooth in the upper jaw, FIG. 9B shows a plane 83 that is tangential to a point 83A on a tooth of the upper jaw 84. In this case, point 83A is provided at the center of the facial surface of the canine tooth, although point 83A may be provided at any suitable location of any suitable tooth. Plane 83 may be graphically provided in a three-dimensional Cartesian coordinate system 85, in which the origin of the coordinate system 85 (i.e., the (0,0,0) point) is disposed at point 83A. The Y-axis is provided in the mesial-distal direction of the jaw, the X-axis is provided perpendicular to the Y-axis and in the occlusal plane, and the Z-axis extends perpendicular to the XY-plane and in the sagittal plane. In the XY-plane, an angle R may be formed between the Y-axis and the intersection line of plane 83 and the XY-plane. This intersection line may be considered as a line that is tangent to a point on a tooth of the upper jaw in the mesial-distal direction.

Figure 9C:
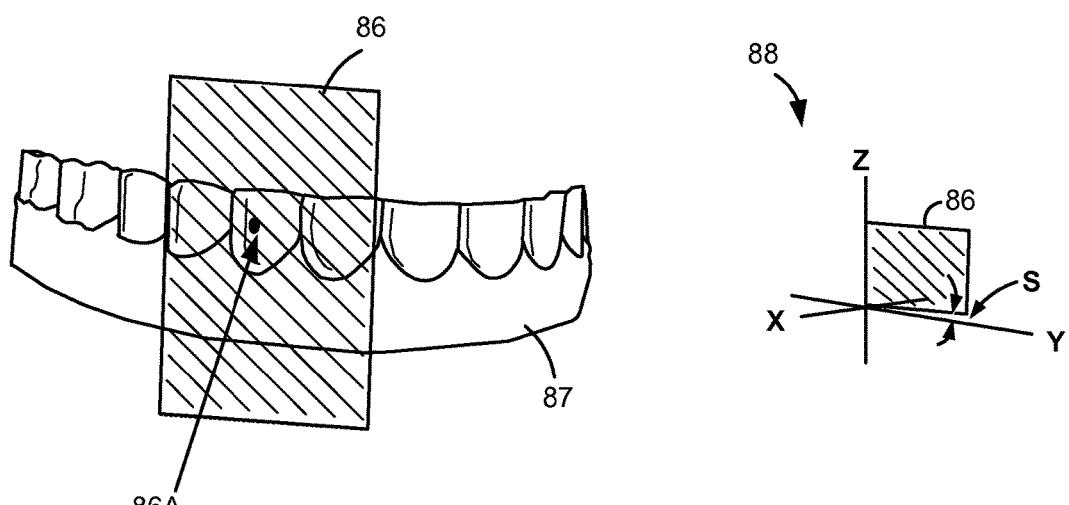
FIG. 9C shows a plane that is tangential to a point on a tooth of the lower jaw.

With respect to a corresponding tooth in the lower jaw, FIG. 9C shows a plane 86 that is tangential to a point 86A on a tooth of the lower jaw 87. In this case, point 86A is provided at the center of the facial surface of the canine tooth, although point 86A may be provided at any suitable point and tooth that corresponds to the point and tooth chosen for the upper jaw. Like plane 83, plane 86 may be graphically provided in a three-dimensional Cartesian coordinate system 88, but in this case the origin of the coordinate system 88 is disposed at point 86A, and an angle S is formed between the Y-axis and the intersection line of plane 86 and the XY-plane. This intersection line may be considered as a line that is tangent to a point on a tooth of the lower jaw in the mesial-distal direction.

Figure 9D:
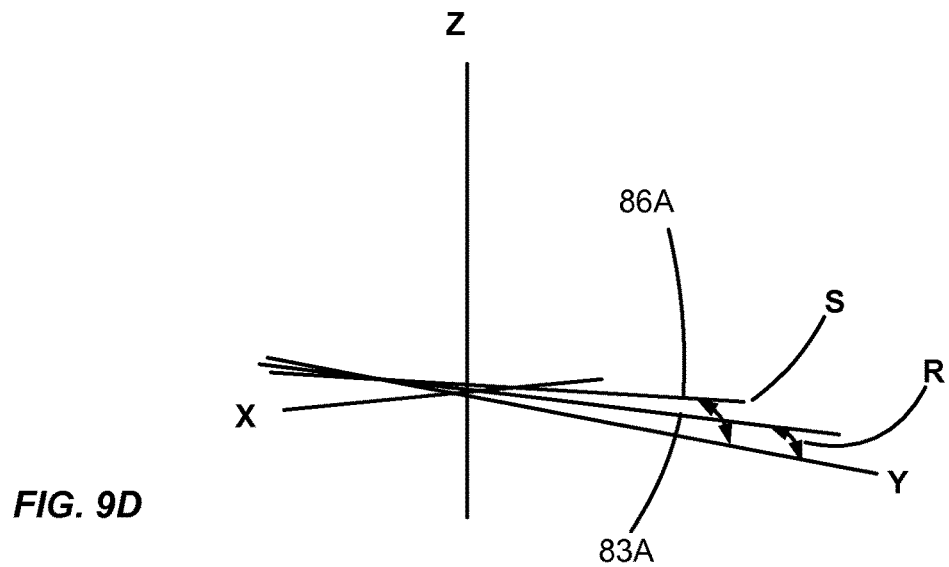
FIG. 9D shows the tangent lines (i.e., intersection lines) for each of the upper and lower jaws drawn on a common Cartesian coordinate system.
Figure 9E:
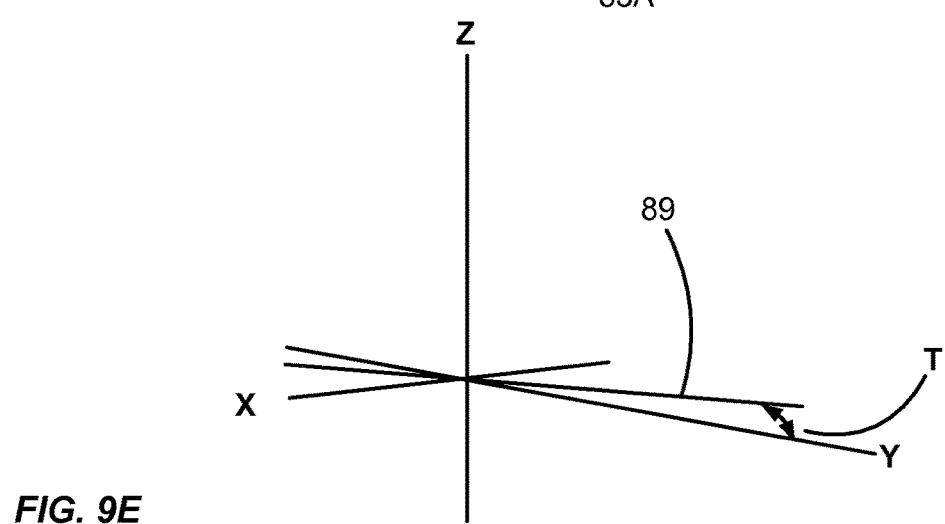
FIG. 9E shows the average line of tangent lines.

The average direction line of the tangent lines may then be determined. For example, FIG. 9D shows the tangent lines (i.e., intersection lines) for each of the upper and lower jaws drawn on a common Cartesian coordinate system. Intersection line 83A is the line representing the intersection line of plane 83 and the XY-plane, while intersection line 86A is the line representing the intersection line of plane 86 and the XY-plane. FIG. 9E shows the average line 89 of the tangent lines. The average line 89 is determined by drawing a line at an angle T from the Y-axis, where the angle T is equal to the average of angle R and angle S.

Figure 9F:
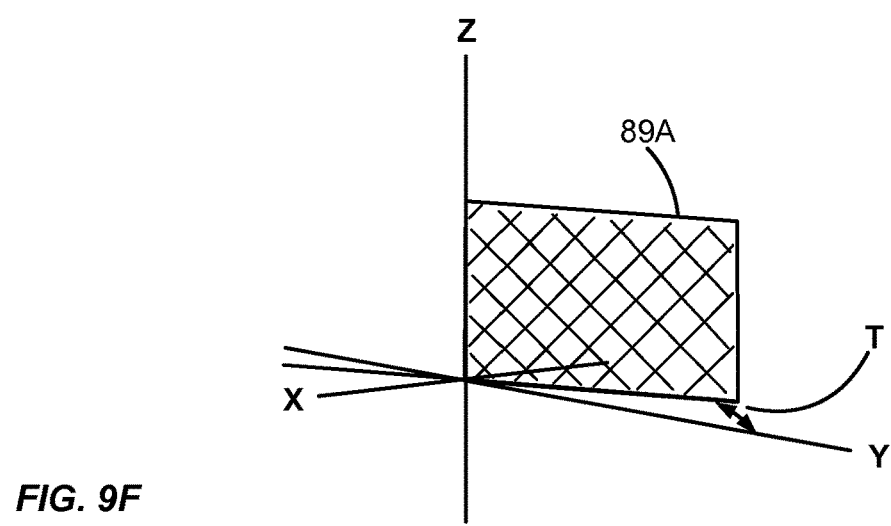
FIG. 9F shows a measurement plane formed using an average line.

A measurement plane may then be generated using the average direction line determined from the tangent lines. For example, FIG. 9F shows a measurement plane 89A formed using average line 89. In this case, measurement plane 89A extends in the Z-plane and passes through average line 89. The measurement plane may represent a plane that is the average of tangential planes 83 and 86, where the average is the average of the direction that each of tangential planes 83 and 86 are arranged in the mesial-distal direction.

Figure 9G:
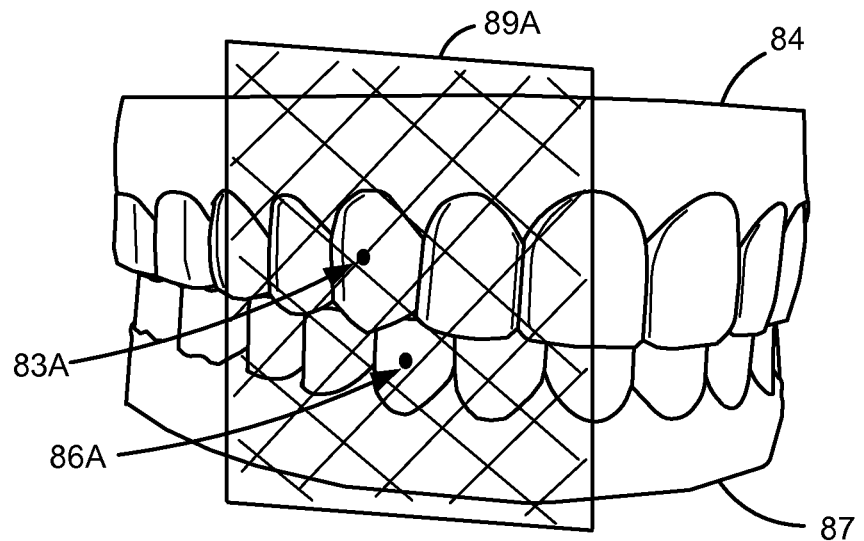
FIG. 9G shows a measurement plane disposed proximate to the upper jaw and lower jaw when the patient's mouth is closed.
Figure 9H:
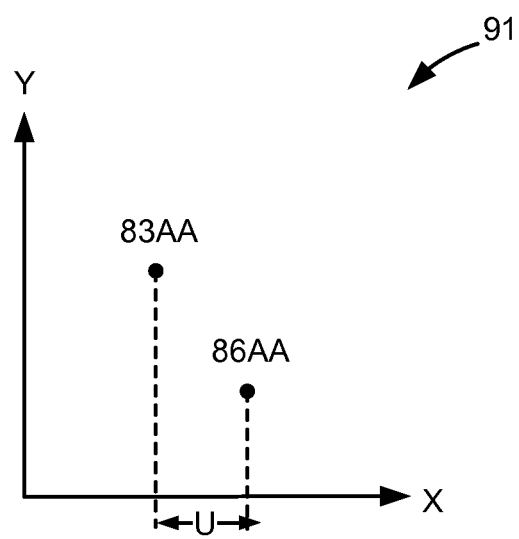
FIG. 9H shows a plane represented as a two-dimensional Cartesian coordinate system.

A distance between points 83A and 86A may then be determined using the measurement plane 89a. For example, FIG. 9G shows measurement plane 89A disposed proximate to upper jaw 84 and lower jaw 87 when the patient's mouth is closed. Measurement plane 89A may be arranged between points 83A and 86A, or at any other suitable location. Points 83A and 86A may then be projected onto plane 89A. For example, FIG. 9H shows plane 89A represented as a two-dimensional Cartesian coordinate system 91. The X-axis is in the mesial-distal direction and the Y-axis is perpendicular to the X-axis. Point 83A is projected onto plane 89A as point 83AA, and point 86A is projected onto plane 89A as point 86AA. A distance U between points 83AA and 86AA along the X-axis may then be determined and subsequently used for determining whether patient has a malocclusion and, in some cases, the type of malocclusion.

Turning back to FIG. 7, in operation 66, a determination is made as to whether the distance is within an allowable range. If it is determined that the distance is within an allowable range, then no malocclusion is detected as shown in operation 67. On the other hand, if it is determined that distance is not within the allowable range, a malocclusion is detected as shown in operation 68.

The allowable range may be any suitable range for defining a malocclusion, and may include different ranges for identifying different types of malocclusions as well as different severity levels of the malocclusions. In one embodiment and with reference to FIG. 8A, the distance between points A and B may be less than −6 mm, and thus it may be determined that the patient has a Class III type malocclusion (distocclusion). One of ordinary skill in the art would recognize that this range is merely exemplary, and other ranges suitable for identifying a Class III type malocclusion may be used. For example, a Class III type malocclusion may be identified if the distance between points A and B is less than −5 mm, −5.5 mm, −6.5 mm, −7 mm, or is less than a value in the range −5 mm to −7 mm.

In one embodiment and with reference to FIG. 8B, the distance between points A and B may be between −6 mm and 0 mm, and thus it may be determined that the patient has a Class I type malocclusion (neutrocclusion). One of ordinary skill in the art would recognize that this range is merely exemplary, and other ranges suitable for identifying a Class I type malocclusion may be used. For example, a Class I type malocclusion may be identified if the distance between points A and B is greater than −5 mm, −5.5 mm, −6.5 mm, −7 mm, or a value in the range −5 mm to −7 mm, and less than −1 mm, −0.5 mm, 0.5 mm, 1 mm, or a value in the range −1 mm to 1 mm.

In one embodiment and with reference to FIG. 8C, the distance between points A and B may be greater than 0 mm, and thus it may be determined that the patient has a Class III type malocclusion (mesiocclusion). One of ordinary skill in the art would recognize that this range is merely exemplary, and other ranges suitable for identifying a Class III type malocclusion may be used. For example, a Class III type malocclusion may be identified if the distance between points A and B is greater than −1 mm, −0.5 mm, 0.5 mm, 1 mm, or a value in the range −1 mm to 1 mm.

In some embodiments, in determining that no malocclusion is detected (operation 67), it may be determined that no specific types of malocclusion is detected. For example, in operation 66, it may be determined whether the distance between points A and B is between −6 mm and 0 mm. In this case, it may be determined that no malocclusion is detected in that neither distocclusion nor mesiocclusion are detected. If it is determined that the distance between points A and B is either less than −7 mm or greater than 0 mm, a malocclusion (i.e., distocclusion or mesiocclusion) may be detected.

It should be appreciated that method 60 may be implemented by any suitable electronic computing device, server, or system. A system that may be used in accordance with one embodiment is discussed later with reference to FIG. 18. Further, the specific operations illustrated in FIG. 7 provide a particular method of detecting dental malocclusions, according to certain embodiments of the present invention. Other sequences of operations may also be performed according to alternative embodiments. For example, alternative embodiments of the present invention may perform the operations outlined above in a different order. Moreover, the individual operations illustrated in FIG. 7 may include multiple sub-operations that may be performed in various sequences as appropriate to the individual operations. Furthermore, additional operations may be added or existing operations removed depending on the particular applications. One of ordinary skill in the art would recognize and appreciate many variations, modifications, and alternatives.

In some embodiments, methods for designing patient removable orthodontic tooth positioning appliances may be provided, and in some cases may be provided as part of an overall orthodontic treatment method such as that discussed with reference to FIG. 6. For example, if a malocclusion is detected using a technique such as that discussed with reference to operation 44 of FIG. 6, computer-based 3-dimensional planning/design tools, such as Treat™ software from Align Technology, Inc., may be used to design and subsequently fabricate tooth positioning appliances. In designing the tooth positioning appliances, the 3-dimensional planning/design tool may be used to place a digital representation of an elastic band receiving member (such as an orthodontic button) on a digital representation of a patient's tooth. Based on the shape, size, and/or orientation of the elastic band receiving member with respect to the patient's tooth, the 3-dimensional planning/design tool may generate a cutout line. The cutout line may subsequently be used to assist in fabricating the tooth positioning appliance, in that it may define a line for cutting the appliance such that the appliance does not interfere with the elastic band receiving member when the appliance is disposed over the patient's teeth.

Figure 10:
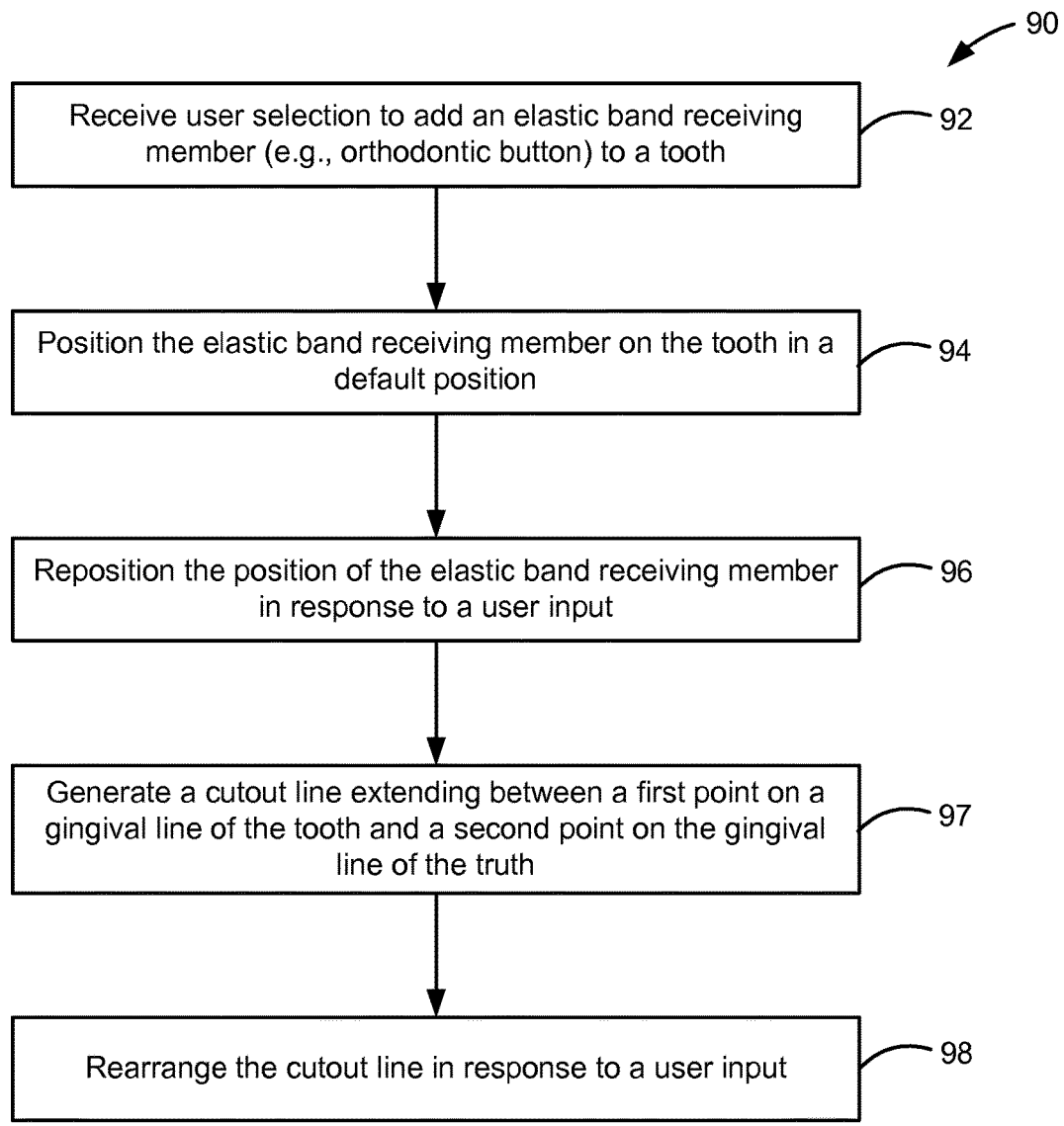
FIG. 10 is a simplified block diagram illustrating a method for designing a patient removable orthodontic tooth positioning appliance including a cutout.

FIG. 10 is a simplified block diagram illustrating a method 90 for designing a patient removable orthodontic tooth positioning appliance including a cutout. In one embodiment, the operations depicted and discussed with reference to method 90 may correspond to the provision for a button placement of operation 48 discussed with reference to FIG. 6. Accordingly, a digital representation of a patient's teeth arrangement may initially be acquired, as discussed with reference to operation 42 of FIG. 6.

In operation 92, a user selection to add an elastic band receiving member (e.g., an orthodontic button) to a tooth is received. In some embodiments, geometry information describing the geometries of one or more orthodontic elastic band receiving members may be stored in the computer-based planning/design tool, and the user may use a graphical user interface (GUI) to select one of the elastic band receiving members and its corresponding geometry. In one embodiment, after selecting the elastic band receiving member, the user may be able to modify properties of the elastic band receiving member, such as size, shape, etc. In other embodiments, the user may be able to upload to the computer-based planning/design tool geometry information describing the geometry of a custom elastic band receiving member, and subsequently use the custom elastic band receiving member for designing the tooth positioning appliance.

In receiving the user selection to add an elastic band receiving member to a tooth, computer-based planning/design tool also receives a user selection of a particular tooth and tooth surface. For example, the user may select a molar, a premolar, an incisor, or any other suitable tooth. In some embodiments, computer-based planning/design tool may provide a default tooth surface. For example, in response to the user selecting a particular tooth, the elastic band receiving member may be added to a facial surface of the selected tooth. In one embodiment, the user may select the tooth surface on which the elastic band receiving member is to be added, such as a facial surface, a lingual surface, or any other suitable surface.

Figure 11A:
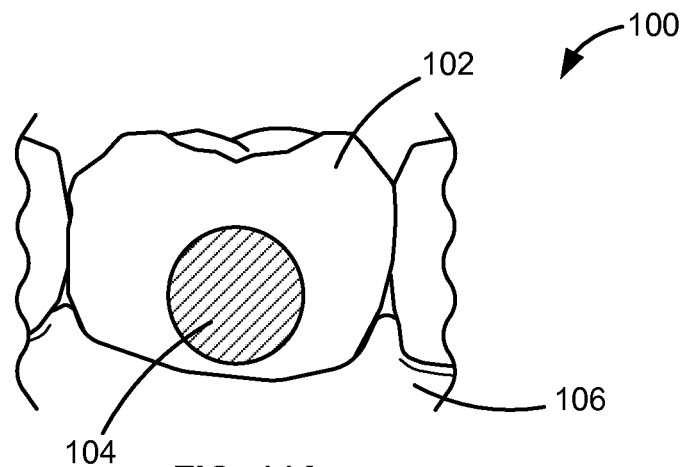
FIG. 11A shows a simplified digital representation of a patient's tooth having an elastic band receiving member disposed thereon.

FIG. 11A shows a simplified digital representation 100 of a patient's tooth 102 having an elastic band receiving member 104 disposed thereon. Digital representation 100 may include teeth other than tooth 102, or may include only tooth 102. Further, digital representation 100 may include other dental features as well, such as gingiva 106. In some embodiments, in response to receiving a user selection add an elastic band receiving member to a tooth, digital representation 100 may be displayed to the user, where tooth 102 represents the user-selected tooth and elastic band receiving member 104 represents the user-selected elastic band receiving member.

Turning back to FIG. 10, in operation 94, the elastic band receiving member is positioned on the tooth in a default position. In positioning the elastic band receiving member in a default location, the computer-based planning/design tool may place the elastic band receiving member in any suitable location on the surface of the tooth such that the elastic band receiving member may function as intended. In some embodiments, this may include positioning the elastic band receiving member a distance away from various dental features, such as the gingival line, the occlusal surface, the distal surface, the mesial surface, etc. In one embodiment, this may include positioning the elastic band receiving member in a center of the tooth surface.

Figure 11B:
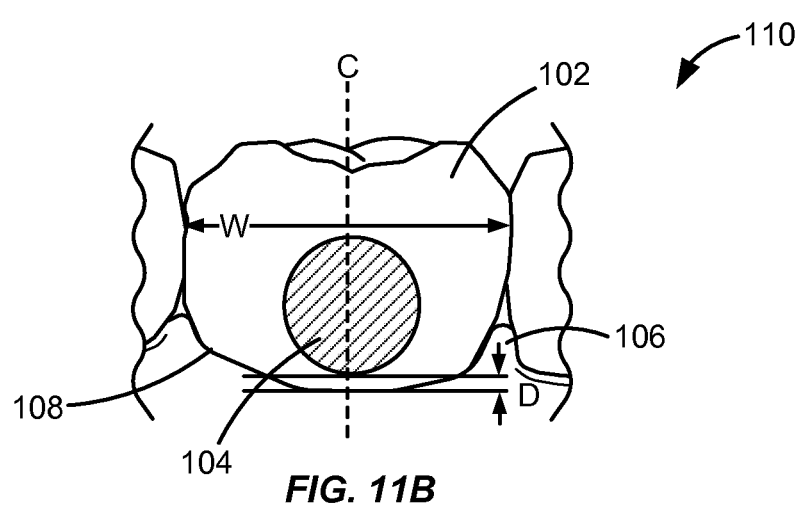
FIG. 11B shows a simplified digital representation of a patient's tooth and an elastic band receiving member with overlaid placement guidelines.

FIG. 11B shows a simplified digital representation 110 of a patient's tooth 102 and an elastic band receiving member 104 with overlaid placement guidelines, where the placement guidelines may be used to determine the default location. In this embodiment, the computer-based planning/design tool may determine a width W of tooth 102, and use W to identify a centerline C (e.g., by dividing W in half). Elastic band receiving member 104 may then be centered about centerline C. Further, a distance D between gingival line 108 and an edge of elastic band receiving member 104 may be defined. For example, D may be 0.5 mm, 1.0 mm, 1.5 mm, in the range of 0.5 to 1.5 mm, less than 0.5 mm, or greater than 1.5 mm. In some embodiments, D may be measured from the intersection point of centerline C and gingival line 108, and may always be greater than 0 mm.

In placing elastic band receiving member 104 in a default position, computer-based planning/design tool may ensure one or more of a variety of placement conditions are satisfied. For example, computer-based planning/design tool may ensure that elastic band receiving member 104 does not contact the gingival line, does not overlap with other teeth, is placed entirely on a single surface of a tooth, etc.

Turning back to FIG. 10, in operation 96, the elastic band receiving member may be repositioned on the tooth in response to a user input. Once the elastic band receiving member has originally been placed, the user may change a position, orientation, or the like of the elastic band receiving member. For example, the user may rotate the elastic band receiving member, move the elastic band receiving member horizontally or vertically, etc. In some embodiments, computer-based planning/design tool may prevent the user from violating one or more of the placement conditions. In other embodiments, computer-based planning/design tool may allow the user to violate or otherwise override one or more of the placement conditions.

Figure 11C:
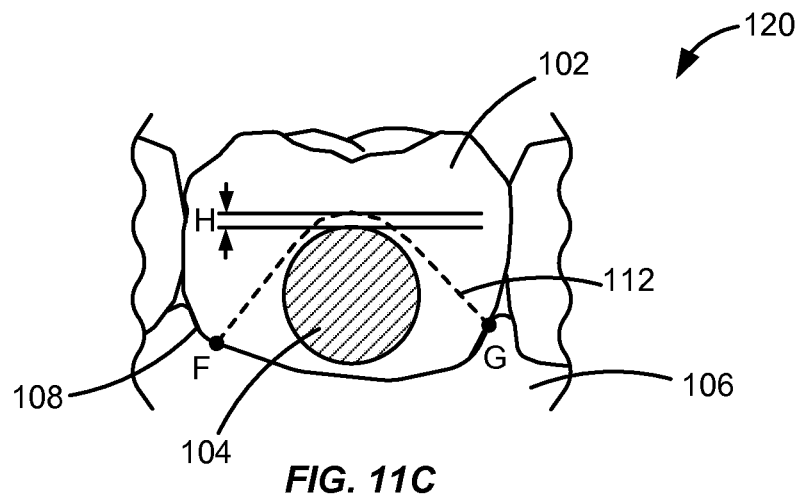
FIG. 11C shows a simplified digital representation of a patient's tooth and an elastic band receiving member with cutout line.

In operation 97, a cutout line is generated, where the cutout line extends between a first point on a gingival line of the tooth and a second point on the gingival line of the tooth. For example, FIG. 11C shows a simplified digital representation 120 of a patient's tooth 102 and an elastic band receiving member 104 with cutout line 112. Cutout line 112 extends between a first point F located on gingival line 108 and a second point G located on gingival line 108. Cutout line 112 may be subsequently used to define a line for cutting a tooth positioning appliance, and specifically for cutting a portion of a tooth positioning appliance that will be disposed over a patient's tooth having an elastic band receiving member attached thereto. Accordingly, cutout line 112 may be any suitable line that, when subsequently used to cut a tooth positioning appliance, results in a tooth positioning appliance that does not interfere with an elastic band receiving member disposed on a patient's tooth. In some embodiments, cutout line 112 may be displayed by computer-based planning/design tool, while in other embodiments cutout line 112 may not be displayed. In at least one embodiment, cutout line 112 may be recalculated in response to a repositioning of elastic band receiving member 104.

In some embodiments, cutout line 112 may be optimized by the computer-based planning/design tool. For example, cutout line 112 may be calculated as the shortest line that extends from the gingival line on one side of elastic band receiving member 104 to the gingival line on the opposite side of elastic band receiving member 104 while passing between elastic band receiving member 104 and an occlusal surface of tooth 102 and not contacting elastic band receiving member 104.

In one embodiment, cutout line 112 may be shaped to conform to at least a portion of the shape of elastic band receiving member 104. For example, with reference to FIG. 11C, elastic band receiving member 104 is circular, and cutout line 112 includes a portion extending between elastic band receiving member 104 and the occlusal surface of the tooth that has a similar radius as the radius of elastic band receiving member 104. In one embodiment, a distance H may be defined between an edge of elastic band receiving member 104 and a portion of cutout line 112. Distance H may be any suitable distance greater than 0 mm, such as 0.5 mm, 1.0 mm, 1.5 mm, in a range from 0.5 mm to 1.5 mm, less than 0.5 mm, or greater than 1.5 mm.

Figure 11D:
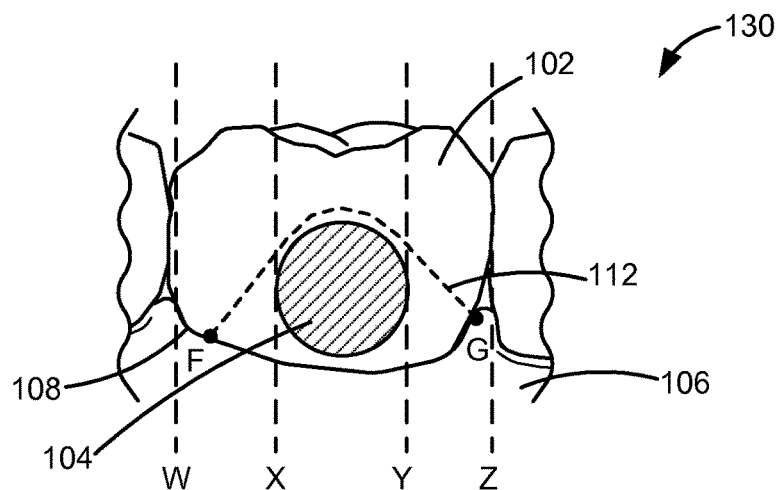
FIG. 11D shows a simplified digital representation of a patient's tooth and an elastic band receiving member with a cutout line and overlaid constraint lines.

In some embodiments, a location of points F and G on gingival line 108 (i.e., the endpoints of cutout line 112) may be constrained. For example, FIG. 11D shows a simplified digital representation 130 of a patient's tooth 102 and an elastic band receiving member 104 with a cutout line and overlaid constraint lines W, X, Y, and Z. Constraint lines W and Z may pass through gingival line 108 at opposite edge of tooth 102, while constraint lines X and Y may pass through gingival line 108 at opposite edges of elastic band receiving member 104. In some embodiments, point F may be limited to a location on gingival line 108 between constraint lines W and X, while point G may be limited to a location on gingival line 108 between constraint lines Y and Z. In other embodiments, points F and G may be limited to a location that is at least a certain distance away from one or more of constraint lines W, X, Y, and Z. For example, point F may be limited to a location that is at least 1 mm away from constraint line W.

In some embodiments, various other conditions may be imposed on cutout line 112, tooth 102, and/or elastic band receiving member 104. For example, cutout line 112 may be required to not intersect with itself. For another example, elastic band receiving member 104 may be limited to an area between gingival line 108 and cutout line 112. For yet another example, surfaces of tooth 102 may not be manipulable.

Turning back to FIG. 10, in operation 98, the cutout line is rearranged in response to a user input. A position, length, shape and/or orientation of the cutout line may be rearranged as desired in accordance with a user input. For example, computer-based planning/design tool may initially generate a cutout line based on a shape and position of an elastic band receiving member and one or more constraints, and may then subsequently allow a treating practitioner to alter the default cutout line as desired.

Figure 11E:
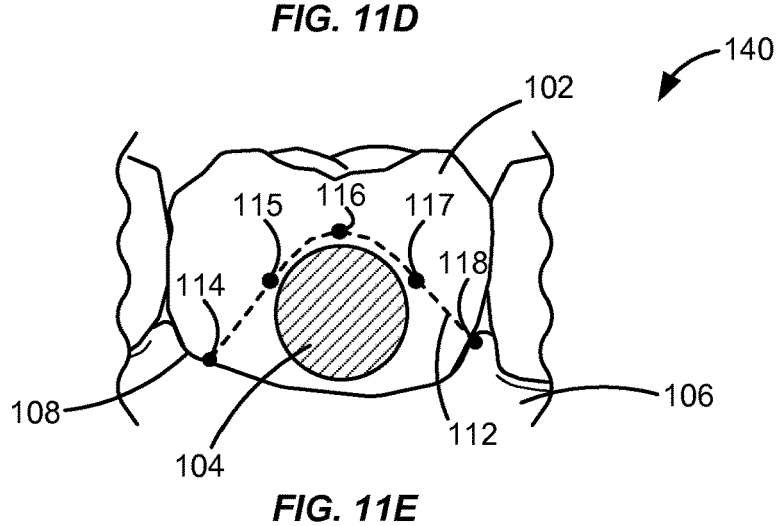
FIG. 11E shows a simplified digital representation of a patient's tooth and an elastic band receiving member with a cutout line having user-manipulable nodes.
Figure 11F:
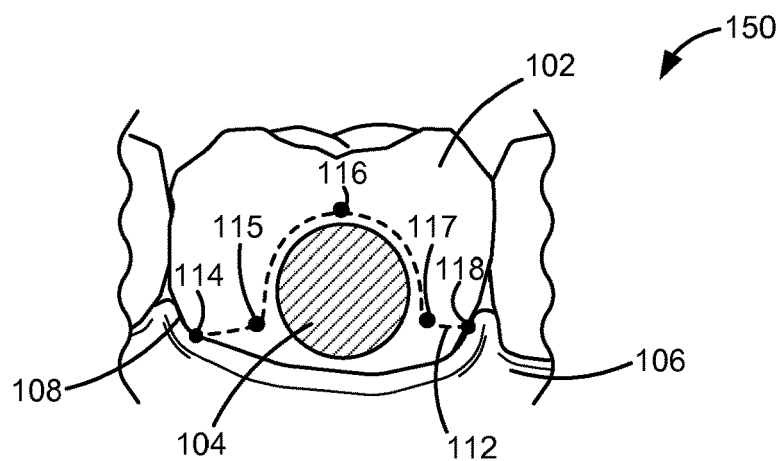
FIG. 11F shows a simplified digital representation of a patient's tooth and an elastic band receiving member with a manipulated cutout line.

In one embodiment, nodes may facilitate the rearrangement of the cutout line. For example, FIG. 11E shows a simplified digital representation 140 of a patient's tooth 102 and an elastic band receiving member 104 with a cutout line having user-manipulable nodes 114-118. One or more user-manipulable nodes may be provided, where the nodes operate to segment the cutout line into a plurality of connected lines having shapes that are user-manipulable. In this embodiment, five nodes are shown. A user may reposition a node such as node 116, whereby repositioning the node may result in the lines to adjacent nodes (e.g., the cutout line between nodes 115 and 116, and the cutout line between nodes 116 and 117) being adjusted. For example, FIG. 11F shows a simplified digital representation 150 of a patient's tooth 102 and an elastic band receiving member 104 with a manipulated cutout line 112. In this case, nodes 115 and 117 have been repositioned to a location closer to gingival line 108.

Figure 11G:
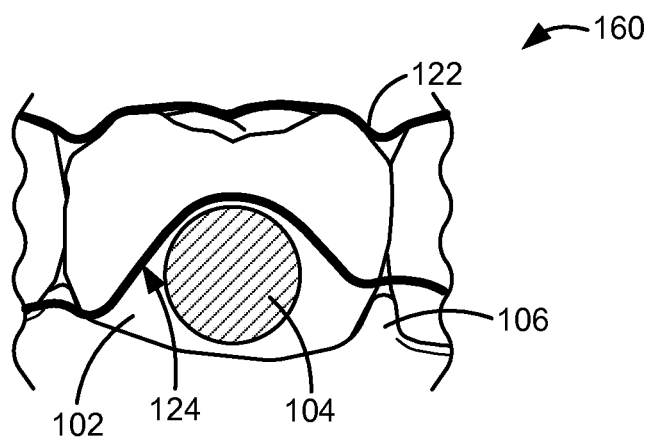
FIG. 11G is a simplified representation of an orthodontic tooth positioning appliance disposed over a tooth having an elastic band receiving member disposed thereon.

Once the cutout line has been generated, the cutout line may be used to fabricate an orthodontic tooth positioning appliance. For example, FIG. 11G is a simplified representation 160 of an orthodontic tooth positioning appliance 122 disposed over a tooth 102 having an elastic band receiving member 104 attached thereto. Orthodontic tooth positioning appliance 122 includes a cutout 124, where cutout 124 has a shape defined by the generated cutout line. In this example, cutout 124 has a shape defined by cutout line 122 discussed with reference to FIGS. 11C, 11D, and 11E. Accordingly, it may be recognized that cutout line 112 and subsequently cutout line 122 may define a gingival-facing surface of orthodontic tooth positioning appliance 122.

It should be appreciated that method 90 may be implemented by any suitable electronic computing device, server, or system. A system that may be used in accordance with one embodiment is discussed later with reference to FIG. 18. Further, the specific operations illustrated in FIG. 10 and also discussed with reference to FIGS. 11A to 11G provide a particular method of designing a patient removable orthodontic tooth positioning appliance, according to certain embodiments of the present invention. Other sequences of operations may also be performed according to alternative embodiments. For example, alternative embodiments of the present invention may perform the operations outlined above in a different order. Moreover, the individual operations illustrated in FIG. 10 and also discussed with reference to FIGS. 11A to 11G may include multiple sub-operations that may be performed in various sequences as appropriate to the individual operations. Furthermore, additional operations may be added or existing operations removed depending on the particular applications. One of ordinary skill in the art would recognize and appreciate many variations, modifications, and alternatives.

In some embodiments, in addition or alternatively to placing a digital representation of an elastic band receiving member on a digital representation of a patient's tooth and using the digital representation of the elastic band receiving member to generate a cutout line, computer-based planning/design tool may generate a cutout line for defining a hook to be fabricated in the orthodontic tooth positioning appliance. This may include receiving user inputs for identifying a tooth and tooth surface to place the hook, as well as user inputs for reshaping a default cutout line.

Figure 12:
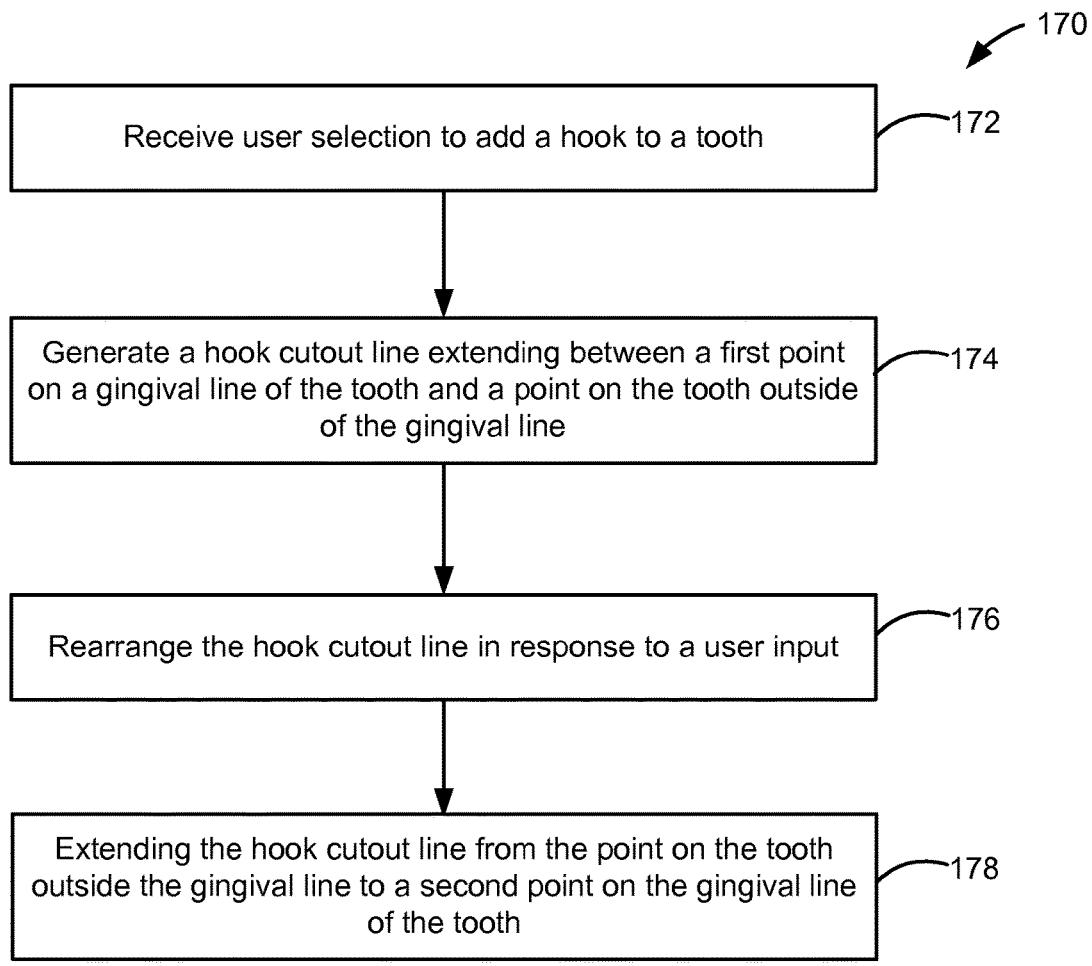
FIG. 12 is a simplified block diagram illustrating a method for designing a patient removable orthodontic tooth positioning appliance including a hook.

FIG. 12 is a simplified block diagram illustrating a method 170 for designing a patient removable orthodontic tooth positioning appliance including a hook. In one embodiment, the operations depicted and discussed with reference to method 170 may correspond to the provision for a hook placement of operation 50 discussed with reference to FIG. 6. Accordingly, a digital representation of a patient's teeth arrangement may initially be acquired, as discussed with reference to operation 42 of FIG. 6.

In operation 172, a user selection to add a hook (e.g., a portion of a patient-removable tooth positioning appliance operable to receive an elastic band) to a tooth is received. Operation 172 may be similar to operation 92 discussed with reference to FIG. 10, but in this case the user selection is to add a hook rather than an elastic band receiving member. Accordingly, the user may select a particular tooth and tooth surface to add a hook.

Figure 13A:
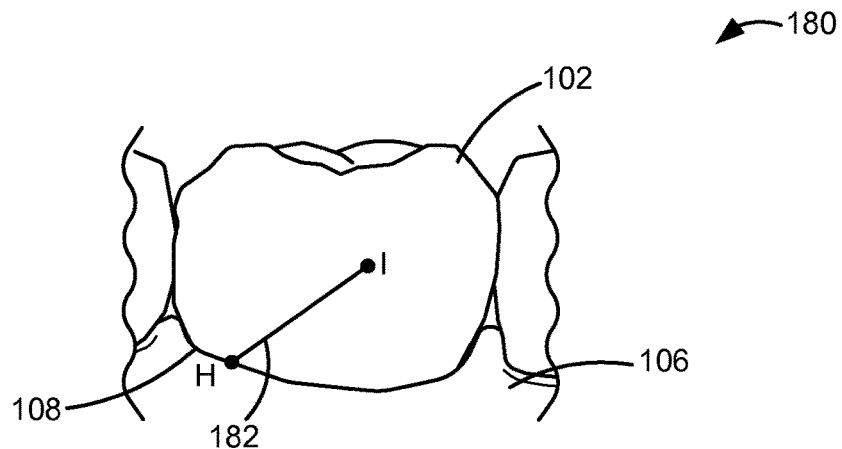
FIG. 13A shows a simplified digital representation of a patient's tooth having a cutout line for a hook disposed thereon.

In operation 174, computer-based planning/design tool generates a hook cutout line extending between a first point on a gingival line of the tooth and a point on the tooth outside of the gingival line. For example, FIG. 13A shows a simplified digital representation 180 of a patient's tooth 102 having a cutout line 182 for a hook disposed thereon. Digital representation 180 may include teeth other than tooth 102, or may include only tooth 102. Further, digital representation 180 may include other dental features as well, such as gingiva 106. In some embodiments, in response to receiving a user selection to add a hook to a tooth, digital representation 180 may be displayed to the user, where tooth 102 represents the user-selected tooth and cutout line 182 represents a portion of a cutout line that may be used to define a hook in a fabricated tooth positioning appliance. Cutout line 182 extends between point H located on gingival line 108 and point I which is located on a surface of tooth 102 but not on gingival line 108.

Figure 13B:
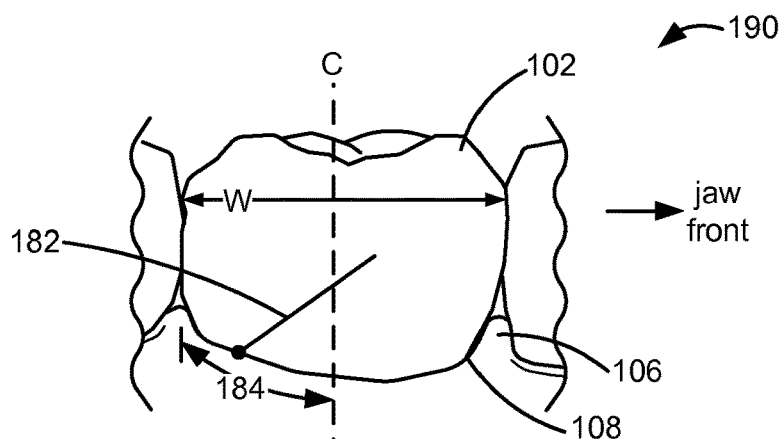
FIG. 13B shows a simplified digital representation of a patient's tooth having a cutout line disposed in a first orientation.

In some embodiments, the cutout line may be positioned in a default location. In positioning the cutout line in a default location, computer-based planning/design tool may orient the cutout line in any direction on the surface of the tooth such that a resulting hook may function as intended. For example, FIG. 13B shows a simplified digital representation 190 of a patient's tooth 102 having a cutout line 182 disposed in a first orientation. For purposes of explanation, cutout line 182 may be said to point in a distal direction, in which case a resulting hook formed in an orthodontic positioning appliance may have an opening facing the distal direction. Although not shown, the cutout line may alternatively be pointed in a mesial direction.

In some embodiments, default hook orientations may be associated with each tooth. For example, for molars and second pre-molars, default hook orientations may be orientations in the distal direction. For first pre-molars, canines, and incisors, default hook orientations may be orientations in the mesial direction. These associations may be stored by computer-based planning/design tool such that in response to a user selecting a particular tooth to add a hook, the default hook orientation may be determined.

In some embodiments, once a hook orientation is determined, a location of the hook may be determined. For example, with reference to FIG. 13B, computer-based planning/design tool may determine the width of tooth 102 and centerline C. Computer-based planning/design tool may then identify a portion 184 of gingival line 108 on which an end point of cutout line 182 may be located. In one embodiment, portion 184 of gingival line 108 may be located between centerline C and an edge of tooth 102. In response to determining a distal-oriented hook, computer-based planning/design tool may locate an end of cutout line 182 somewhere along (e.g., at the center of) portion 184 of gingival line 108.

Figure 13C:
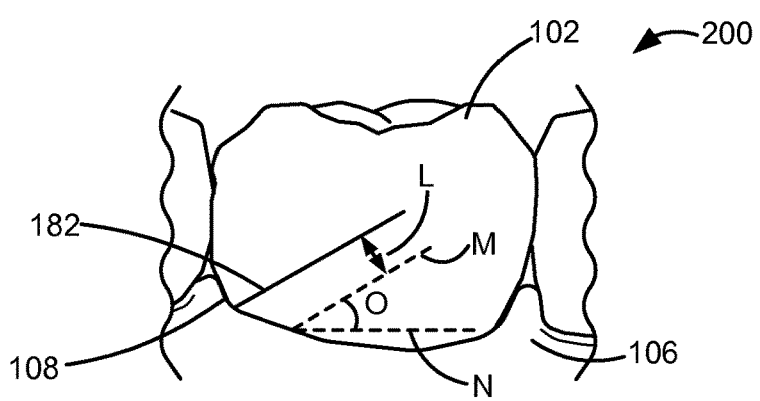
FIG. 13C shows a simplified digital representation of a patient's tooth and geometrical information for a cutout line.

In some embodiments, geometry information describing the geometry of the hook may be stored in the computer-based planning/design tool and provide a default location and orientation of the hook cutout. For example, FIG. 13C shows a simplified digital representation 200 of a patient's tooth 102 and geometrical information for a cutout line 182. The geometrical information includes a slit offset L, a hook width M, a hook length N, and a hook angle O. Default values for the geometrical information may be stored by computer-based planning/design tool and used to provide a default size and orientation of the hook cutout. For example L may be 0.5 mm, 0.75 mm, 1 mm, in the range from 0.5 mm to 1 mm, less than 0.5 mm, or greater than 1 mm. M may be 1 mm, 2 mm, 3 mm, in a range from 1 mm to 3 mm, less than 1 mm or greater than 3 mm. N may be 1 mm, 2 mm, 3 mm, in a range from 1 mm to 3 mm, less than 1 mm or greater than 3 mm. O may be 30 degrees, 45 degrees, 60 degrees, in a range from 30 degrees to 60 degrees, less than 30 degrees or greater than 60 degrees.

In placing hook cutout 182 in a default position, computer-based planning/design tool may ensure one or more of a variety of placement conditions are satisfied. For example, computer-based planning/design tool may ensure that hook cutout 182 is oriented in a particular direction based on the type of tooth it is disposed over, does not extend to an occlusal surface of the tooth, does not extend to gingival line 182, does not intersect with itself, etc.

Turning back to FIG. 12, in operation 176, the hook cutout line may be rearranged in response to a user input. Once the hook cutout line has originally been placed, the user may change a position, orientation, or the like of the hook cutout line. For example, the user may change one or more of slit offset L, hook width M, hook length N, hook angle O, and a location of point H (FIGS. 13B and 13C). In some embodiments, computer-based planning/design tool may prevent the user from violating one or more of the placement conditions. In other embodiments, computer-based planning/design tool may allow the user to violate or otherwise override one or more of the placement conditions.

Figure 13D:
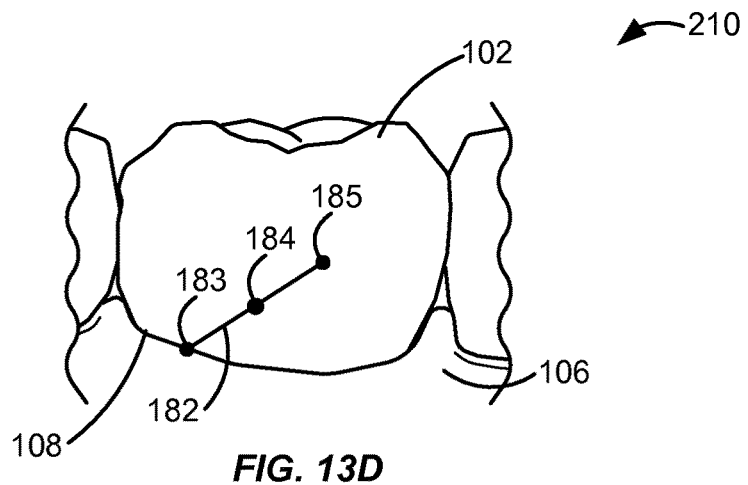
FIG. 13D shows a simplified digital representation of a patient's tooth and a hook cutout line having user-manipulable nodes.
Figure 13E:
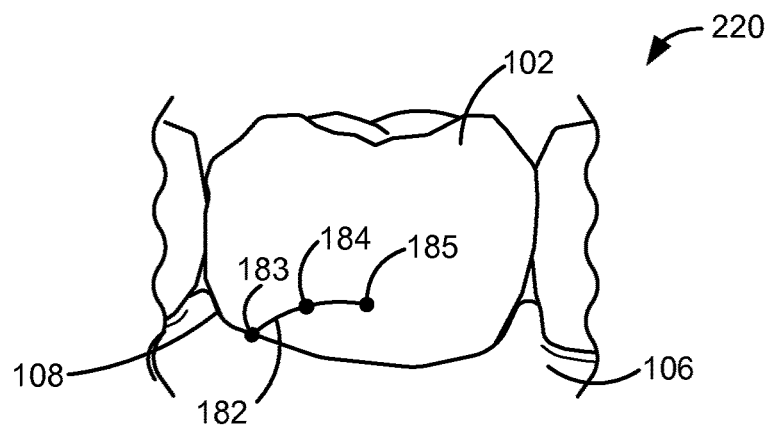
FIG. 13E shows a simplified digital representation of a patient's tooth and a manipulated hook cutout line according to a first embodiment.
Figure 13F:
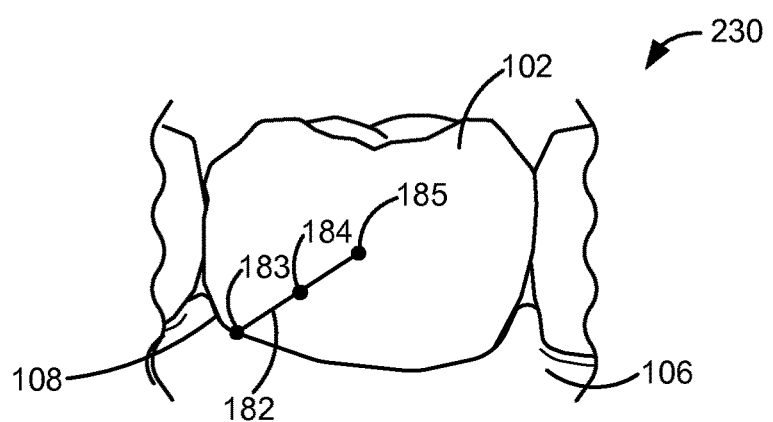
FIG. 13F shows a simplified digital representation of a patient's tooth and a manipulated hook cutout line according to a second embodiment.

In one embodiment, nodes may facilitate the rearrangement of the hook cutout line. For example, FIG. 13D shows a simplified digital representation 210 of a patient's tooth 102 and a hook cutout line 182 having user-manipulable nodes 183-185. User-manipulable nodes 183-185 may be similar to user-manipulable nodes 114-118 discussed with reference to FIG. 11E. In this case, a user may use user-manipulable nodes 183-185 to modify a shape of hook cutout line 182. For example, FIG. 13E shows a simplified digital representation 220 of a patient's tooth 102 and a manipulated hook cutout line 182 according to a first embodiment. In this case, nodes 184 and 185 have been repositioned to a location closer to gingival line 108. For another example, FIG. 13F shows a simplified digital representation 230 of a patient's tooth 102 and a manipulated hook cutout line 182 according to a second embodiment. In this case, hook cutout line 182 has been linearly shifted to a location closer to an edge of tooth 102.

Figure 13G:
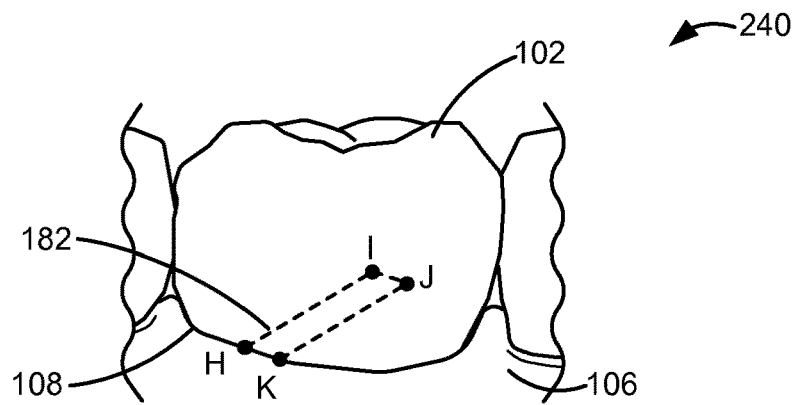
FIG. 13G shows a simplified digital representation of a patient's tooth and an extended cutout line according to a first embodiment.

Turning back to FIG. 12, in operation 178, the hook cutout line may be extended from the point on the tooth outside the gingival line to a second point on the gingival line of the tooth. In extending the hook cutout line back to the gingival line, the entire hook may be defined. For example, FIG. 13G shows a simplified digital representation 240 of a patient's tooth 102 and an extended cutout line 182 according to a first embodiment. Extended cutout line 182 includes an extension from point I to a point K on gingival line 108. In this case, the extension passes through an additional point J.

Figure 13H:
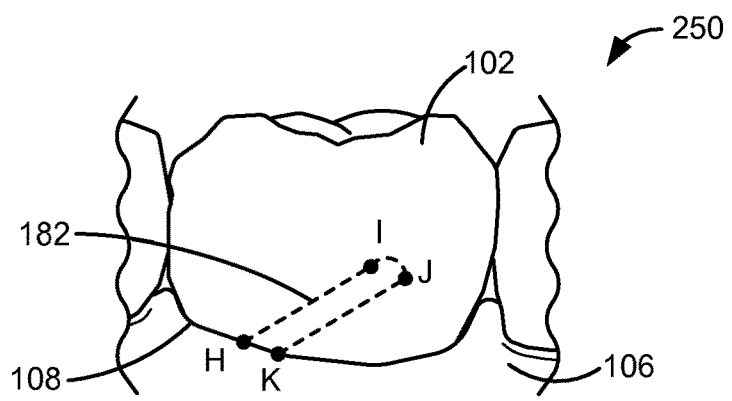
FIG. 13H shows a simplified digital representation of a patient's tooth and an extended cutout line according to a second embodiment.

The extension from point I to point K may have any suitable shape and length. In one embodiment, as shown in FIG. 13G, the extension includes a first portion extending between points I and J and a second portion extending between points J and K. Further, the second portion extending between points J and K is in parallel with the portion extending between points H and I, and is provided at a distance from the portion extending between points H and I based on slit offset L (FIG. 13C). In this embodiment, the portion extending from point I to point J is linear. However, this portion may assume one or more curves. For example, FIG. 13H shows a simplified digital representation 250 of a patient's tooth 102 and an extended cutout line 182 according to a second embodiment. In this case, the portion extending between points I and J is a curved line rather than a straight line.

Figure 13I:
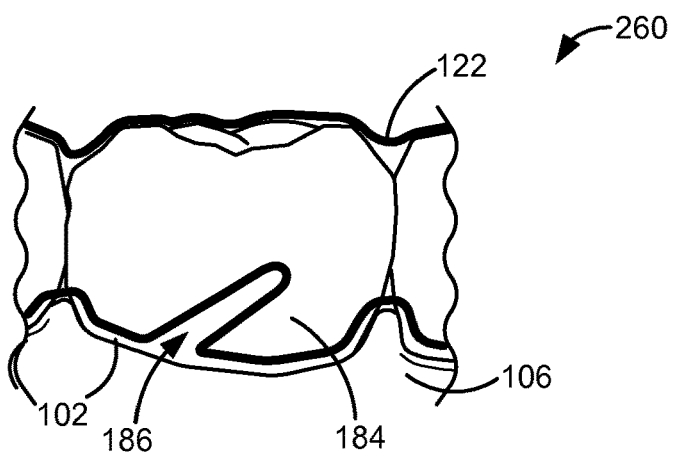
FIG. 13I is a simplified representation of an orthodontic tooth positioning appliance disposed over a tooth having a hook formed therein.

Once the hook cutout line has been generated, the cutout line may be used to fabricate an orthodontic tooth positioning appliance. For example, FIG. 13I is a simplified representation 260 of an orthodontic tooth positioning appliance 122 disposed over a tooth 102 and having a hook formed therein. Orthodontic tooth positioning appliance 122 includes a cutout 186, where cutout 186 has a shape defined by the extended hook cutout line. In this example, cutout 186 has a shape defined by extended cutout line 182 discussed with reference to FIG. 13H. Accordingly, it may be recognized that cutout line 182 may define a surface of orthodontic tooth positioning appliance 122 operable to receive an elastic band.

It should be appreciated that method 170 may be implemented by any suitable electronic computing device, server, or system. A system that may be used in accordance with one embodiment is discussed later with reference to FIG. 18. Further, the specific operations illustrated in FIG. 12 and also discussed with reference to FIGS. 13A to 13I provide a particular method of designing a patient removable orthodontic tooth positioning appliance, according to certain embodiments of the present invention. Other sequences of operations may also be performed according to alternative embodiments. For example, alternative embodiments of the present invention may perform the operations outlined above in a different order. Moreover, the individual operations illustrated in FIG. 12 and also discussed with reference to FIGS. 13A to 13I may include multiple sub-operations that may be performed in various sequences as appropriate to the individual operations. Furthermore, additional operations may be added or existing operations removed depending on the particular applications. One of ordinary skill in the art would recognize and appreciate many variations, modifications, and alternatives.

In some embodiments, an orientation of a hook cutout line may be optimized based on a location of an elastic band receiving member. In some embodiments, the location of the elastic band receiving member may be identified by an actual elastic band receiving member (such as elastic band receiving member 12 of FIG. 2) or a digital representation of the elastic band receiving member on a tooth (such as elastic band receiving member 104 of FIGS. 11A to 11F). In other embodiments, the location of the elastic band receiving member may be identified by an actual cutout from an tooth positioning appliance (such as cutout 124 of FIG. 11G) or a digital representation of the cutout (such as cutout line 112 of FIGS. 11C to 11F). The orientation may be determined so that an elastic band can be functionally disposed over the elastic band receiving member and the hook and, in some embodiments, may be determined as part of operation 174 or operation 176 discussed with reference to FIG. 12.

Figure 14:
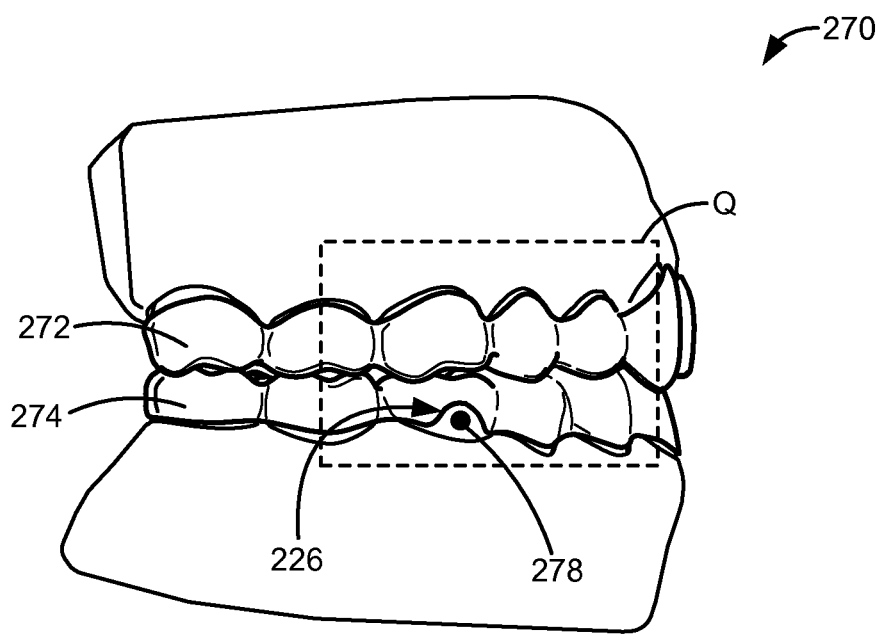
FIG. 14 is a side view of patient's mouth including a tooth positioning device requiring a hook.

FIG. 14 is a side view of patient's mouth 270 including a tooth positioning device requiring a hook. The tooth positioning device includes a first tooth positioning appliance 272 for disposal on teeth of the patient's upper jaw, and a second tooth positioning appliance 274 for disposal on teeth of the patient's lower jaw. In this embodiment, second tooth positioning appliance 274 includes a cutout 276 to prevent interference with an elastic band receiving member 278 disposed on a tooth of the patient's lower jaw. Accordingly, it may be desirable to provide a hook on first tooth positioning appliance 272 so that an elastic band may be used with the hook and elastic band receiving member 278.

Figure 15A:
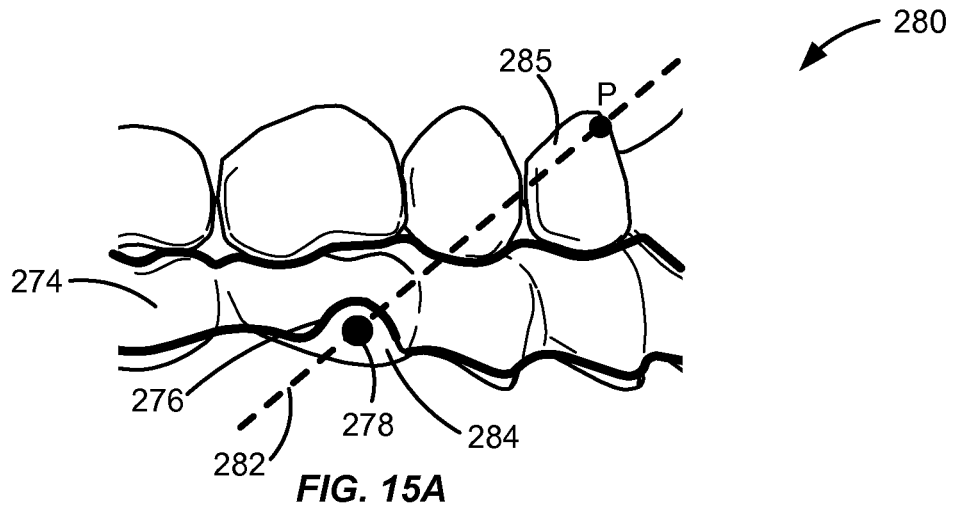
FIG. 15A shows a magnified portion of FIG. 14 without a tooth positioning appliance on the teeth of the patient's upper jaw and including a hook orientation guideline.

FIG. 15A shows a magnified portion Q of FIG. 14 without a tooth positioning appliance on the teeth of the patient's upper jaw and including a hook orientation guideline 282. The computer-based planning/design tool calculates hook orientation guideline 282 as a line extending between a tooth having an elastic band receiving member 278 and a tooth intended to have a hook disposed there over when the patient's mouth is closed. Hook orientation guidelines may then be used to cut a hook into a tooth positioning appliance to be disposed on the tooth of the patient's upper jaw.

In one embodiment, hook orientation guideline 282 passes through a center of elastic band receiving member 278. One of ordinary skill in the art would recognize that hook orientation guideline 282 need not pass through the exact center of elastic band receiving member 278, but rather could pass through an area in the proximity of elastic band receiving member 278, such as an area defined by tooth surface 284. Further, this point may be calculated using one or more of elastic band receiving member 278 and cutout 276.

In one embodiment, hook orientation guideline 282 passes through a point P located on the gingival line of the tooth over which a hook is to be provided. In some embodiments, point P may be the same as point H (FIGS. 13A to 13I). For example, a user may select tooth 285 to dispose a hook over. Once tooth 285 is selected, computer-based planning/design tool may determine the orientation (mesial/distal) of the hook cutout line, and a location of point P. Computer-based planning/design tool may then subsequently generate hook orientation guideline 282 to pass through point P.

Figure 15B:
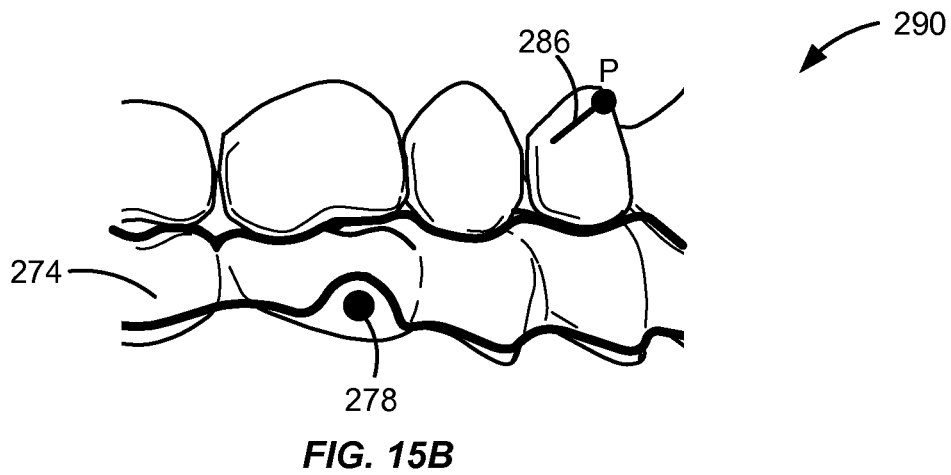
FIG. 15B shows a magnified portion of FIG. 14 without a tooth positioning appliance on the teeth of the patient's upper jaw and including a hook cutout line.

Hook orientation guideline 282 may be used to determine an angle O (FIG. 13C) of a hook cutout line. For example, FIG. 15B shows a magnified portion Q of FIG. 14 without a tooth positioning appliance on the teeth of the patient's upper jaw and including a hook cutout line 286. Hook cutout line 286 extends from point P in a direction along hook orientation guideline 282 toward elastic band receiving member 278.

Figure 15C:
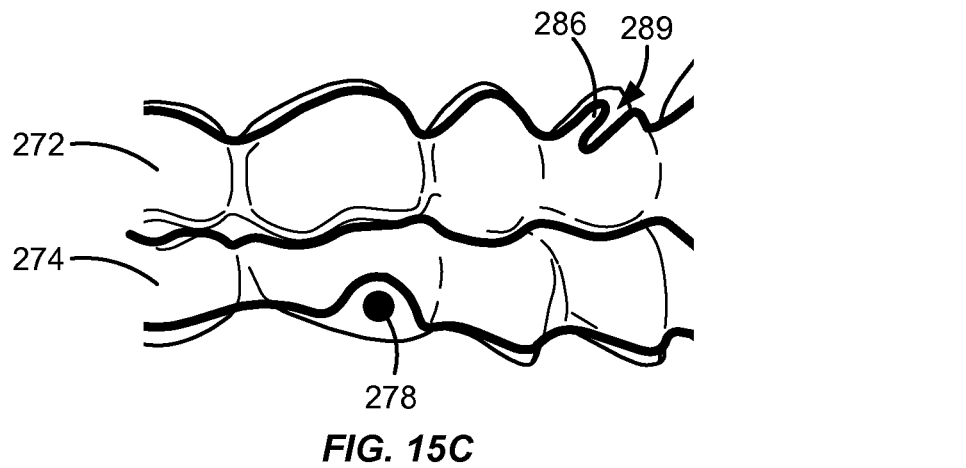
FIG. 15C shows a magnified portion of FIG. 14 where a tooth positioning appliance on the teeth of the patient's upper jaw includes a hook.

Hook cutout line 286 may then be used to fabricate a tooth positioning appliance having a hook oriented in a direction of elastic band receiving member 278. For example, FIG. 15C shows a magnified portion Q of FIG. 14 where a tooth positioning appliance 272 on the teeth of the patient's upper jaw includes a hook 288. A shape of hook 288 is at least partially defined by cutout 289, where cutout 289 has a shape which extends in a substantially linear direction toward elastic band receiving member 278 when the patient's teeth are in occlusion.

In some embodiments, one or more a variety of techniques may be used to fabricate an orthodontic tooth positioning device such as orthodontic positioning device 30 discussed with reference to FIGS. 5A and 5B. In one case, a mold of a patient's teeth may be acquired and subsequently used to create tooth positioning appliances such as tooth positioning appliance 10 discussed with reference to FIG. 1. The tooth positioning appliance may then be trimmed using cutout lines, where the cutout lines may define gingival-facing surfaces of the tooth positioning appliance and, when used, prevent interference with an elastic band receiving member (such as an orthodontic button) and/or make the tooth positioning appliance operable to receive an elastic band (e.g., by providing a hook in the appliance). In another case, a digital representation of the tooth positioning appliance may be generated, and gingival-facing surfaces of the appliance may be digitally defined using one or more cutout lines. A tooth positioning appliance may then be directly fabricated using the digital representation of the tooth positioning appliance.

Figure 16:
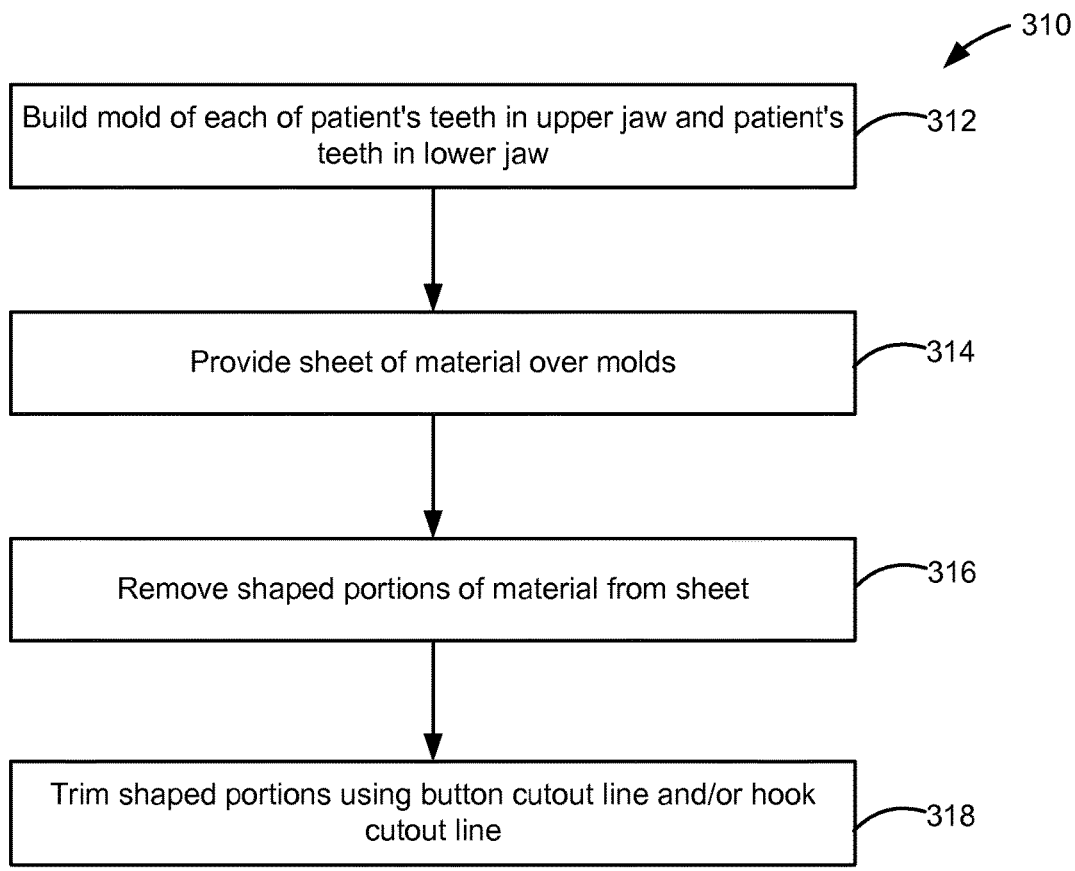
FIG. 16 illustrates a method for fabricating a tooth positioning device in accordance with a first embodiment.

FIG. 16 illustrates a method 310 for fabricating a tooth positioning device in accordance with a first embodiment. It should be appreciated that method 310 can be practiced in a variety of ways. For example, method 310 can be computer implemented and employ three-dimensional modeling representations and techniques.

In operation 312, a mold of a patient's teeth in their upper and lower jaws is built. The mold may be built using any one of a number of known techniques. For example, the mold may be built from a digital representation of the patient's dentition, via the use of dental trays and molding material, or using any other suitable technique. In some embodiments, the mold may include structures corresponding to orthodontic fixtures affixed to the patient's teeth, such as elastic band receiving members.

In operation 314, a sheet of material is provided over the mold. The material may be any suitable material for forming tooth positioning appliances. Examples of specific types of material which may be used include any suitable polymer material, including an elastomeric polymeric material such as Tru-Tain 0.03 in. thermal forming dental material manufactured by Tru-Tain Plastics of Rochester, Minn., and/or a thermoplastic polyurethane material such as Estane manufactured by Lubrizol of Wickliffe, Ohio, and/or a polycarbonate material such as Lexan manufactured by Saudi Basic Industries Corp. of Riyadh, Saudi Arabia, and/or a polyester or copolyester material such as Eastar manufactured by Eastman Corp. of Kingsport, Tenn., and/or a thermoplastic polyolefin material such as Engage manufactured by The Dow Chemical Co. of Midland, Mich.

In providing the sheet of material over the mold, portions of the material may assume the shape of the mold. For example, the mold and material may be provided in a vacuum chamber, whereby application of a vacuum may cause the material to form to the shape of the mold.

In operation 316, shaped portions of material are removed from the sheet. The shaped portions are those portions that were shaped by providing the sheet of material over the mold. The shaped portions may be removed using any known techniques, whereby the shaped portions are roughly cut from the sheet.

In operation 318, the shaped portions are trimmed using a button cutout line and/or a hook cutout line. For example, the shaped portions may be trimmed using cutout line 112 discussed with reference to FIGS. 11C to 11F, and/or using cutout line 182 discussed with reference to FIGS. 13A to 13H, and/or using cutout line 286 discussed with reference to FIG. 15B. The shaped portions may also be trimmed using a gingival line such as gingival line 108 discussed with reference to FIGS. 11B to 11F and FIGS. 13A to 13H. As a result, a gingival-facing surface of the trimmed shaped portions may follow the contours of a patient's gingival line and include cutouts for preventing interference with elastic band receiving members and/or cutouts for defining hooks in the trimmed shaped portions. In trimming the shaped portions, a digital representation of trimming instructions may be received, where the trimming instructions include at least one of the button cutout line and the hook cutout line.

Any one of various techniques for trimming the shaped portions using a cutout line may be used. According to one embodiment, the shaped portions may be arranged over a mold shaped to receive the positioning appliance. A cutting element such as a disk saw may then be applied along a direction normal to a buccal surface or a labial surface of the teeth receiving cavities. While cutting, the cutting element may be retracted from the mold if the cutting element contacts a surface of the mold.

Figure 17:
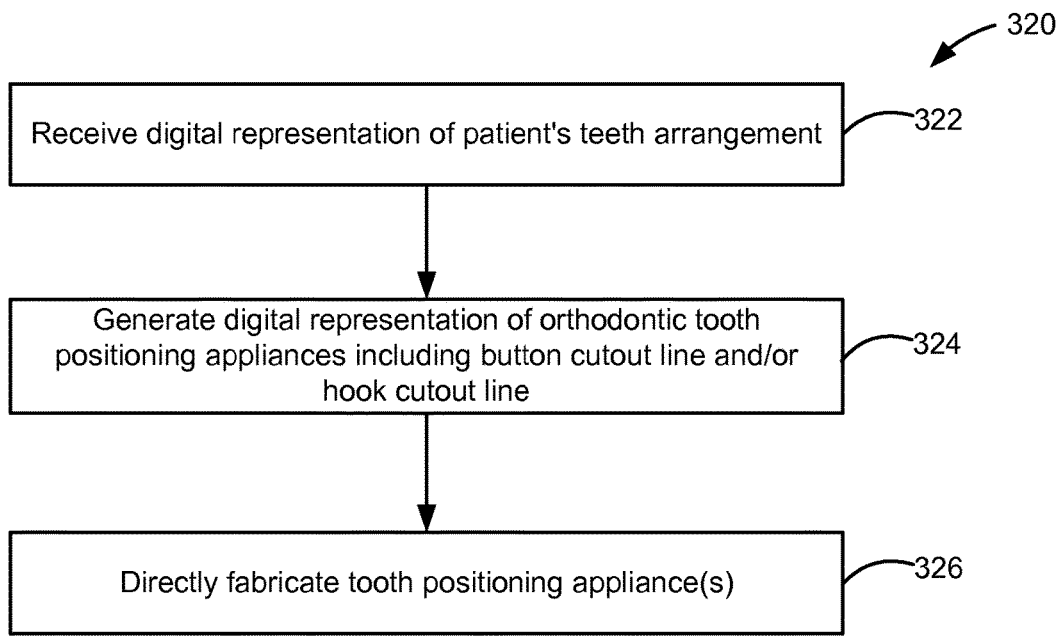
FIG. 17 illustrates a method for fabricating a tooth positioning device in accordance with a second embodiment.

FIG. 17 illustrates a method 320 for fabricating a tooth positioning device in accordance with a second embodiment. It should be appreciated that method 320 can be practiced in a variety of ways. For example, method 320 can be computer implemented and employ three-dimensional modeling representations and techniques.

In operation 322, a digital representation of a patient's teeth is received. In one embodiment, the received digital representation includes a digital representation of one or more orthodontic fixtures such as an elastic band receiving member affixed to a tooth. In another embodiment, the received digital representation is modified to add or remove the digital representation(s) of orthodontic fixture(s). The digital representation may be originally generated in any known fashion. For example, the digital representation may be originally generated by scanning the patient's. Further, the teeth may be in a current arrangement in a different arrangement. For example, the teeth may be provided in or re-arranged to an intermediate or final position.

In operation 324, a digital representation of one or more orthodontic tooth positioning appliances is generated, where the appliances include a button cutout line and/or a hook cutout line. The button cutout line may correspond cutout line 112 discussed with reference to FIGS. 11C to 11F. The hook cutout line may correspond to cutout line 182 discussed with reference to FIGS. 13A to 13H and/or cutout line 286 discussed with reference to FIG. 15B. The digital representation of the appliances may also include a gingival cutout line, where the gingival cutout line may correspond to gingival line 108 discussed with reference to FIGS. 11B to 11F and/or gingival line discussed with reference to FIGS. 13A to 13H. The button cutout line and hook cutout line may be generated using one or more of the methods and techniques previously discussed, and may or may not be displayed to the user. For example, in generating the button cutout line, a digital representation of an elastic band receiving member may first be generated and placed on a tooth, and the button cutout line subsequently formed partially around the elastic band receiving member.

In operation 326, the orthodontic tooth positioning appliances are directly fabricated. Various known manufacturing processes can be used to directly fabricate the orthodontic tooth positioning appliances using the digital representation generated in operation 324. For example, the orthodontic tooth positioning appliances may be formed by a stereolithography fabrication machine, where resin is selectively hardened in the shape of the tracking template. In fabricating the appliances, a digital representation of trimming instructions may be received, where the trimming instructions include at least one of the button cutout line and the hook cutout line.

It should be appreciated that methods 310 and 320 may be implemented by any suitable electronic computing device, server, or system. A system that may be used in accordance with one embodiment is discussed later with reference to FIG. 18. Further, the specific operations illustrated in FIGS. 16 and 17 provide particular methods of fabricating a tooth positioning device, according to certain embodiments of the present invention. Other sequences of operations may also be performed according to alternative embodiments. For example, alternative embodiments of the present invention may perform the operations outlined above in a different order. Moreover, the individual operations illustrated in FIGS. 16 and 17 may include multiple sub-operations that may be performed in various sequences as appropriate to the individual operations. Furthermore, additional operations may be added or existing operations removed depending on the particular applications. One of ordinary skill in the art would recognize and appreciate many variations, modifications, and alternatives.

Figure 18:
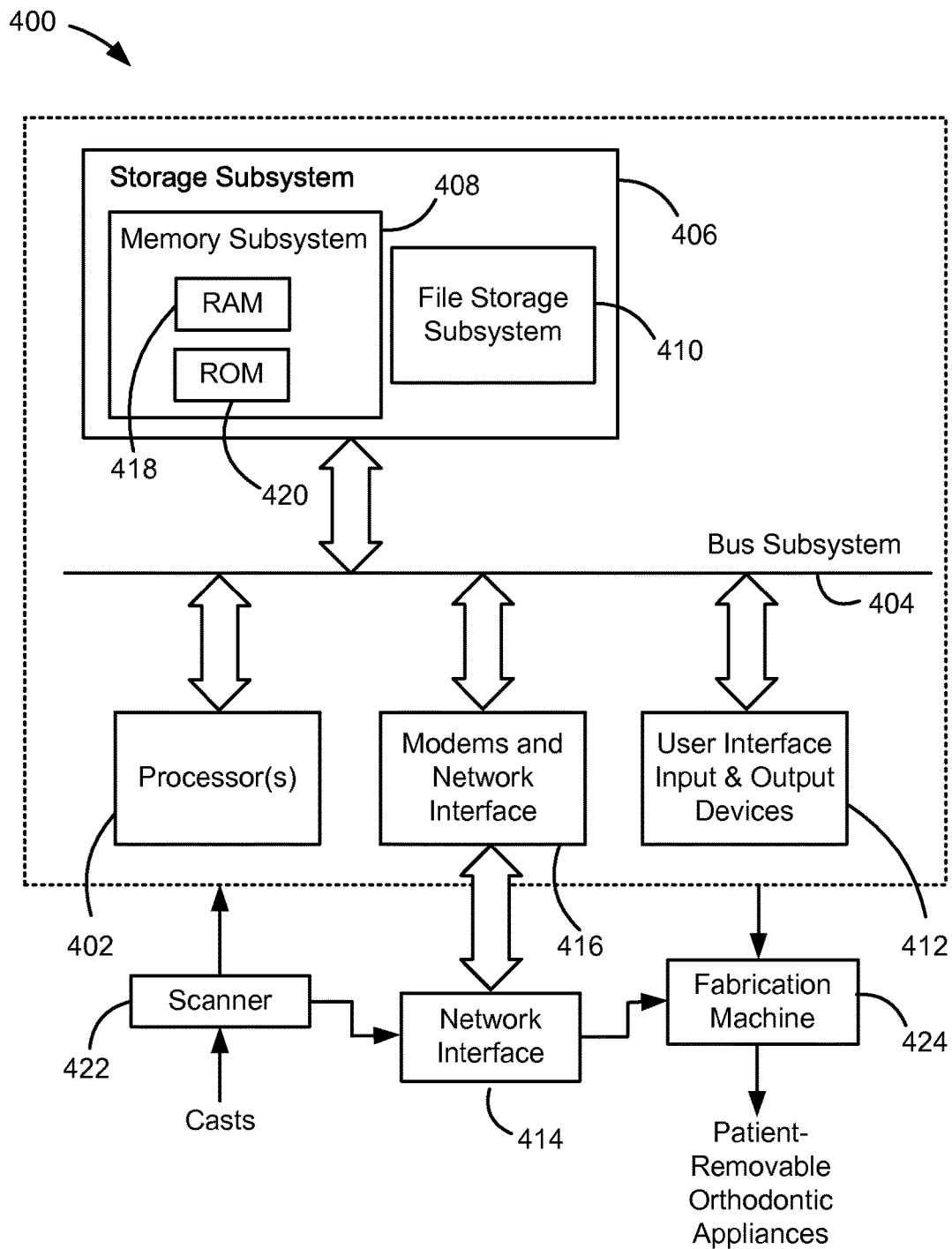
FIG. 18 is a simplified block diagram of a data processing system embodying embodiments of the present invention.

FIG. 18 is a simplified block diagram of a data processing system 400 embodying embodiments of the present invention. Data processing system 400 typically includes at least one processor 402 which communicates with a number of peripheral devices via a bus subsystem 404. These peripheral devices typically include a storage subsystem 406 (memory subsystem 408 and file storage subsystem 410), a set of user interface input and output devices 412, and an interface to outside networks 414, including the public switched telephone network. This interface is shown schematically as "Modems and Network Interface" block 414, and is coupled to corresponding interface devices in other data processing systems via a communication network interface 416. Data processing system 400 could be a terminal or a low-end personal computer or a high-end personal computer, workstation, or mainframe.

The user interface input devices typically include a keyboard and may further include a pointing device and a scanner. The pointing device may be an indirect pointing device such as a mouse, trackball, touchpad, or graphics tablet, or a direct pointing device such as a touch screen incorporated into the display. Other types of user interface input devices, such as voice recognition systems, are also possible.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 406 maintains the basic programming and data constructs that provide the functionality of embodiments of the present invention. Software modules used to implement the methods discussed above are typically stored in storage subsystem 406. Storage subsystem 406 typically comprises memory subsystem 408 and file storage subsystem 410.

Memory subsystem 408 typically includes a number of memories including a main random access memory (RAM) 418 for storage of instructions and data during program execution and a read only memory (ROM) 420 in which fixed instructions are stored. In the case of Macintosh-compatible personal computers the ROM would include portions of the operating system; in the case of IBM-compatible personal computers, this would include the BIOS (basic input/output system).

File storage subsystem 410 provides persistent (non-volatile) storage for program and data files, and typically includes at least one hard disk drive and at least one disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of PCs and workstations.

Bus subsystem 404 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 422 is responsible for scanning impressions or casts of the patient's teeth obtained either from the patient or from an orthodontist and providing the scanned digital data set information to data processing system 400 for further processing. According to some embodiments, canner 422 may operate to directly scan a patient's teeth and, in some cases, orthodontic fixtures such as elastic band receiving members affixed to the patient's teeth. In a distributed environment, scanner 422 may be located at a remote location and communicate scanned digital data set information to data processing system 400 via network interface 416.

Fabrication machine 424 may fabricate patient-removable orthodontic appliances based on tooth arrangement information received from data processing system 400. According to some embodiments, fabrication machine 424 may fabricate the patient-removable orthodontic appliances based on a tooth arrangement and, in some cases, information received from data processing system 400. In a distributed environment, fabrication machine 424 may be located at a remote location and receive data set information from data processing system 400 via network interface 416.

One or more structures as described herein may be provided in the form of a kit. For example, a kit may contain one or more of a patient-removable orthodontic appliance or plurality (e.g., set) of patient-removable orthodontic appliances (including pairs of appliances for simultaneously use with upper and lower jaws where one of the appliances includes a hook and the other appliance includes a cutout for preventing interference with a elastic band receiving member affixed to a patient's tooth). A tooth-receiving cavity of a patient-removable orthodontic appliance can be treated or altered, e.g., by chemical means, so as to affect a property of the appliance. A kit can be configured for delivery to an intended recipient (e.g., patient, practitioner, etc.) directly or indirectly. A kit can include an object or component provided separated from an appliance, but which is meant to be coupled with another component. For example, the kit may also include elastic band receiving members and/or elastic bands.

The software components or functions described in this application may be implemented as software code to be executed by one or more processors using any suitable computer language such as, for example, Java, C++ or Perl using, for example, conventional or object-oriented techniques. The software code may be stored as a series of instructions, or commands on a computer-readable medium, such as a random access memory (RAM), a read-only memory (ROM), a magnetic medium such as a hard-drive or a floppy disk, or an optical medium such as a CD-ROM. Any such computer-readable medium may also reside on or within a single computational apparatus, and may be present on or within different computational apparatuses within a system or network.

The present invention can be implemented in the form of control logic in software or hardware or a combination of both. The control logic may be stored in an information storage medium as a plurality of instructions adapted to direct an information processing device to perform a set of steps disclosed in embodiments of the present invention. Based on the disclosure and teachings provided herein, a person of ordinary skill in the art will appreciate other ways and/or methods to implement the present invention.

The use of the terms "a" and "an" and "the" and similar referents in the context of describing embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope unless otherwise claimed. No language in the specification should be construed as indicating any non-claimed element as essential to the practice of at least one embodiment.

Preferred embodiments are described herein, including the best mode known to the inventors. Variations of those preferred embodiments may become apparent to those of ordinary skill in the art upon reading the foregoing description. The inventors expect skilled artisans to employ such variations as appropriate, and the inventors intend for embodiments to be constructed otherwise than as specifically described herein. Accordingly, suitable embodiments include all modifications and equivalents of the subject matter recited in the claims appended hereto as permitted by applicable law. Moreover, any combination of the above-described elements in all possible variations thereof is contemplated as being incorporated into some suitable embodiment unless otherwise indicated herein or otherwise clearly contradicted by context. The scope of the invention should, therefore, be determined not with reference to the above description, but instead should be determined with reference to the pending claims along with their full scope or equivalents.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An orthodontic system for positioning a patient's teeth, comprising:
   a first patient removable orthodontic tooth positioning appliance having teeth receiving cavities shaped to receive and apply a resilient positioning force to a patient's teeth provided in one of an upper jaw and a lower jaw, the appliance comprising a hook configured to receive an orthodontic elastic band; and
   a second patient removable orthodontic tooth positioning appliance having teeth receiving cavities shaped to receive and apply a resilient positioning force to a patient's teeth provided in the other of the upper jaw and the lower jaw, the appliance comprising a cutout operable to expose an orthodontic elastic band receiving member wherein the cutout is operable to be disposed over a tooth, is shaped to extend between a first point of a gingival line of the tooth and a second point of the gingival line of the tooth, and has a gingival-facing surface arrangeable between the elastic band receiving member and an occlusal surface of the tooth.

2. The system of claim 1, wherein at least a portion of the gingival-facing surface is shaped to conform to the shape of at least a portion of the elastic band receiving member.

3. The system of claim 1, wherein the hook has a shape at least partially defined by a hook cutout in the first patient removable orthodontic tooth positioning appliance, where the hook cutout extends in a linear direction toward the elastic band receiving member when the patient's teeth are in occlusion.

4. The system of claim 3, wherein the hook cutout is a gingival-facing cutout of the orthodontic positioning appliance.

5. The system of claim 1, wherein the hook is shaped to follow a contour of a patient's teeth.

6. The system of claim 1, wherein the cutout defines a gingival-facing opening in the orthodontic positioning appliance.

7. The system of claim 1, wherein the cutout is shaped to avoid interference with elastic band receiving member.

* * * * *